US007838000B2

(12) United States Patent
Scott et al.

(10) Patent No.: US 7,838,000 B2
(45) Date of Patent: Nov. 23, 2010

(54) INHIBITION OF PATHOGENIC AGENTS INCLUDING α6β1 INTEGRIN RECEPTOR OR α6β4 INTEGRIN RECEPTOR AT A SURFACE

(75) Inventors: Thomas R. Scott, Central, SC (US); Heather P. Borick, Clemson, SC (US); Ginger A. Swire-Clark, Easley, SC (US); William R. Marcotte, Jr., Pendleton, SC (US); Ashby B. Bodine, Clemson, SC (US)

(73) Assignee: Clemson University Research Foundation, Clemson, SC (US)

( * ) Notice: Subject to any disclaimer, the term of this patent is extended or adjusted under 35 U.S.C. 154(b) by 333 days.

(21) Appl. No.: 11/440,746

(22) Filed: May 25, 2006

(65) Prior Publication Data

US 2006/0275256 A1 Dec. 7, 2006

Related U.S. Application Data

(63) Continuation of application No. 10/817,423, filed on Apr. 2, 2004, now abandoned.

(51) Int. Cl.
*A61K 39/00* (2006.01)
*A61K 38/00* (2006.01)
(52) U.S. Cl. .................................... 424/184.1; 514/2
(58) Field of Classification Search ....................... None
See application file for complete search history.

(56) References Cited

U.S. PATENT DOCUMENTS

| | | | |
|---|---|---|---|
| 5,266,328 A | 11/1993 | Skubitz et al. | |
| 5,538,725 A | 7/1996 | Imhof | |
| 5,567,440 A * | 10/1996 | Hubbell et al. | 424/484 |
| RE36,844 E | 8/2000 | Jones et al. | |
| 6,114,316 A | 9/2000 | Ramamurthy et al. | |
| 6,294,356 B1 | 9/2001 | Jones et al. | |
| 2002/0058336 A1 * | 5/2002 | Ashkar | 435/368 |
| 2002/0160497 A1 | 10/2002 | Montano et al. | |
| 2002/0168363 A1 | 11/2002 | Feige et al. | |
| 2003/0044899 A1 | 3/2003 | Tryggvason et al. | |
| 2003/0044913 A1 | 3/2003 | Yue et al. | |
| 2003/0091569 A1 | 5/2003 | Gerritsen et al. | |
| 2003/0100529 A1 | 5/2003 | Tryggvason et al. | |
| 2003/0108540 A1 | 6/2003 | Kalluri | |

FOREIGN PATENT DOCUMENTS

WO      WO 02/30465      *    4/2002

OTHER PUBLICATIONS

Cochlovius et al. Therapeutic Antibodies, after years of promise, magic bullets appear to be on the upswing. Modern Drug discovery, 2003, pp. 33-34 and 37-38.*
Abstract of Article—*Form and function: The laminin family of heterotrimers*, Holly Colognato and Peter D. Yurchenco from interscience.wiley.com (2 pages) originally in Developmental Dynamics, vol. 218, Issue 2, 2000, pp. 213-234.
Abstract of Article—*High expression level of alpha 6 integrin in human breast carcinoma is correlated with reduced survival*, K. Friedrichs, P. Ruiz, F. Franke, I. Gille, H. J. Terpe, and B. A. Imhof from cancerres.aacrjournals.org (3 pages) originally in Cancer Research, vol. 51, Issue 4, pp. 901-906.
Abstract of Article—*Identification of integrin-dependent and -independent cell adhesion domains in COOH-terminal globular region of laminin-5 alpha 3 chain*, H. Mizushima, H. Takamura, Y. Miyagi, Y. Kikkawa, N. Yamanaka, H. Yasumitus, K. Misugi, and K. Miyazaki from cgd.aacrjournals.org (4 pages) originally in Cell Growth & Differentiation, vol. 8, Issue 9, 1997, pp. 979-987.
Abstract of Article—*Integrin activation controls metastasis in human breast cancer*, B. Felding-Habermann, T. E. O'Toole, J. W. Smith, E. Fransvea, Z. M. Ruggeri, M. H. Ginsberg, P. E. Hughes, N. Pampori, S. J. Shattil, A. Saven, and B. M. Mueller from ncbi.nlm.nih.gov (2 pages) originally in Proc. Natl, Acad. Sci., vol. 98, No. 4, Feb. 13, 2001, pp. 1853-1858.
Abstract of Article—*Integrin Laminin Receptors and Breast Carcinoma Progression*, Kathleen L. Connor, Jun Chung, Robin E. Bachelder, Arthur M. Mercurio, Isaac Rabinovitz, Leslie M. Shaw, and Taneli Tani from infotrieve.com (1 page) originally in Journal of Mammary Gland Biology and Neoplasi, vol. 6, No. 3, 2001, pp. 299-309.
Abstract of Article—*Localization of heparin binding activity in recombinant laminin G domain*, U. Sung, J. J. O'Rear, and P. D. Yurchenco from ncbi.nlm.nih.gov (1 page) originally in Eur. J. Biochem., vol. 250, No. 1, Nov. 15, 1997, pp. 138-143.
Abstract of Article—*Molecular cloning of the cDNA encoding human laminin A chain*, T. Haaparanta, J. Uitto, E. Ruoslahti, and E. Engvall from ncbi.nlm.nih.gov (2 pages) originally in Matrix, vol. 11, No. 3, Jun. 1991, pp. 151-160.
Abstract of Article—*The integrin alpha 6 beta 1 promotes the survival of metastatic human breast carcinoma cells in mice*, U. M. Wewer, L. M. Shaw, R. Albrechtsen, and A. M. Mercurio from ajp.amjpathol.org (3 pages) originally in American Journal of Pathology, vol. 151, No. 5, 1997, pp. 1191-1198.
Article—*A Novel Design of Targeted Endocrine and Cytokine Therapy for Breast Cancer*, Zhang et al., Clinical Cancer Research, vol, 8, Apr. 2002, pp. 1196-1205.
Article—*A Unique Sequence of the Laminin a3 G Domain Binds to Heparin and Promotes Cell Adhesion through Syndecan-2 and -4*, Atsushi Utani, Motoyoshi Nomizu, Hiroshi Matsuura, Kozue Kato, Takashi Kobayashi, Ushio Takeda, Shinichi Aota, Peter K. Nielsen, and Hiorshi Shinkai, from jbc.org (21 pages) originally in J. Biol. Chem., vol. 276, Issue 31, Aug. 3, 2001, pp. 28779-28788.

(Continued)

*Primary Examiner*—Maher M Haddad
(74) *Attorney, Agent, or Firm*—Dority & Manning, P.A.

(57) ABSTRACT

Disclosed are treatment agents and methods of treatment utilizing the agents directed toward diseases in which the disease causing pathogen includes α6β1 integrin receptors and/or α6β4 integrin receptors on the surface of the pathogen. In one embodiment, the disease can be breast cancer. The therapeutic agents disclosed include a polypeptide comprising at least a portion of the G domain of the laminin-5 α3 chain that has been shown to bind α6β1 integrin receptors and α6β4 integrin receptors. In one embodiment, the therapeutic agents can be fused or chimeric materials in which the laminin-5 α3 chain polypeptide has been chemically bound to another material that can be useful in the destruction or neutralization of the pathogen.

29 Claims, 14 Drawing Sheets

OTHER PUBLICATIONS

Article—*Deposition of laminin 5 in epidermal wounds regulates integrin signaling and adhesion*, Nguyen et al., Current Opinion in Cell Biology, vol. 12, 2000, pp. 554-562.

Article—*Development of a prolactin receptor-targeting fusion toxin using a prolactin antagonist and a recombinant form of Pseudomonas exotoxin A*, Langenheim et al., Breast Cancer Research and Treatment, vol. 90, 2005, pp. 281-293.

Article—*Differential Regulation of Cellular Adhesion and Migration by Recombinant Laminin-5 Forms With Partial Deletion or Mutation Within the G3 Domain of a3 Chain*, Yoshinobu Kariya, Toshiaki Tsubota, Tomomi Hirosaki, Hiroto Mizushima, Wilma Puzon-McLaughlin, Yoshikazu Takada, and Kaoru Miyazaki, Journal of Cellular Biochemistry, vol. 88, 2003, pp. 506-520.

Article—*From genes to protein structure and function: novel applications of computational approaches in the genomic era*, Skolnick et al., Tibtech, vol. 18, Jan. 2000, pp. 34-39.

Article—*Globular domains 4/5 of the laminin a3 chain mediate deposition of precursor laminin 5*, Sigle et al., Journal of Cell Science, vol. 117, No. 19, May 12, 2004, pp. 4481-4494.

Article—*Homozygous a6 integrin mutation in junctional epidermolysis bullosa with congenital duodenal artresia*, Pulkkinen et al., Human Molecular Genetics, vol. 6, No. 5, 1997, pp. 669-674.

Article—*Identification of Integrin-dependent and—independent Cell Adhesion Domains in COOH-Terminal Globular Region of Laminin-5 a3 Chain*, Hiroto Mizushima, Hiroyuki Takamura, Yohei Miyagi, Yamato Kikkawa, Naoki Yamanaka, Hidetaro Yasumitsu, Kazuaki Misugi, and Kaoru Miyazaki, Cell Growth & Differentiation, Vol. 6, Sep. 1997, pp. 979-987.

Article—*IgG Autoantibodies in Patients with Anti-Epiligrin Cicatricial Pemphigoid Recognize the G Domain of the Laminin 5 a-Subunit*, Lazarova et al., Clinical Immunology, vol. 101, No. 1, Oct. 2001, pp. 100-105.

Article—*Immunosuppresive therapy*, Barry D. Kahan, Immunology, vol. 4, 1992, pp. 553-560.

Article—*Isolation and Activity of Proteolytic Fragment of Laminin-5 a3 Chain*, Yoshiaki Tsubota, Hiroto Mizushima, Tomomi Hirosaki, Shouichi Higashi, Hidetaro Yasumitsu, and Kaoru Miyazaki, Biochemical and Biophysical Research Communications, vol. 278, 2000, pp. 614-620.

Article—*Ligand binding to proteins: The binding landscape model*, Miller et al., Protein Science, vol. 6, 1997, pp. 2166-2179.

Article—*Possible Dissociation of the Heparin-binding and Mitogenic Activities of Heparain-binding (Acidic Fibroblast) Growth Factor-1 from Its Receptor-binding Activities by Site-directed Mutagenesis of a Single Lysine Residue*, Burgess et al., The Journal of Cell Biology, vol. 111, 1990, pp. 2129-2138.

Article—*Processing of Laminin-5 and Its Functional Consequences: Role of Plasmin and Tissue-type Plasminogen Activator*, Lawrence E. Goldfinger, M. Sharon Stack, and Jonathan C. R. Jones from jcb.org (28 pages) originally in J. Cell Biol., vol. 141, No. 1, Apr. 6, 1998, pp. 255-265.

Article—*Prolactin Antagonist-endostatin Fusion Protein as a Targeted Dual-Functional Therapeutic Agent for Breast Cancer*, Beck et al., Cancer Research, vol. 63, Jul. 1, 2003, pp. 3598-3604.

Article—*Reversion of the Malignant Phenotype of Human Breast Cells in Three-Dimensional Culture and in Vivo by Integrin Blocking Antibodies*, V. M. Weaver, O. W. Petersen, F. Wang, C. A. Larabell, P. Briand, C. Damsky, and M. J. Bissell from jcb.org (35 pages) originally in J. Cell Biol., vol. 137, No. 1, Apr. 7, 1997, pp. 231-245.

Article—*Spatial Regulation and Activity Modulation of Plamin by High Affinity Binding to the G domain of the $a_3$ Subunit of Laminin-5*, Lawrence E. Goldfinger, Luohua Jiang, Susan B. Hopkinson, M. Sharon Stack, and Jonathan C. R. Jones from jbc.org (14 pages) originally in J. Biol. Chem., vol. 275, Issue 45, Nov. 10, 2000, pp. 34887-34893.

Article—*Structure and assembly of hemidesmosomes*, Jones et al., BioEssays, vol. 20, 1998, pp. 488-494.

Article—*Structure and Function of Hemidesmosomes: More Than Simple Adhesion Complexes*, Borradori et al., The Journal of Investigative Dermatology, vol. 112, No. 4, Apr. 1999, pp. 411-418.

Article—*Structure-Based Strategies for Drug Design and Discovery*, Irwin D. Kuntz, Science, vol. 257, Aug. 21, 1992, pp. 1078-1082.

Article—*Synthetic Peptides Inhibit Adhesion of Human Tumor Cells to Extracellular Matrix Proteins*, Ian B. DeRoock, Michael E. Pennington, Thomas C. Sroka, Kit S. Lam, G. Tim Bowden, Elisabeth L. Bair, and Anne E. Cress from cancerres.aacrjournals.org (15 pages) originally in Cancer Research, vol. 61, Apr. 15, 2001, pp. 3308-3313.

Article—*Targeted Disruption of the LAMA3 Gene in Mice Reveals Abnormalities in Survival and Late Stage Differentiation of Epithelial Cells*, Ryan et al., The Journal of Cell Biology, vol. 145, No. 6, Jun. 14, 1999, pp. 1309-1323.

Article—*The Babel of Bioinformatics*, Teresa K. Attwood, Science, vol. 290, Oct. 20, 2000, pp. 471-473.

Article—*The Functions of Laminins: Lessons from In Vivo Studies*, Ryan et al., Matrix Biology, vol. 15, 1996, pp. 369-381.

Article—*The LG3 Module of Laminin-5 Harbors a Binding Site for Integrin $a_3\beta_1$ That Promotes Cell Adhesion, Spreading, and Migration*, Meiling Shang, Naohiko Koshikawa, Susann Schenk, and Vito Quaranta from jbc.org (21 pages) originally in J. Biol. Chem., vol. 276, Issue 35, Aug. 31, 2001, pp. 33045-33053.

Article—*The SFL activity secreted by metastic carcinoma cells is related to laminin 5 and mediates cell scattering in an integrin-independent manner*, M. Grassi, G. Moens, P. Rousselle, J. P. Thiéry, and J. Jouanneau, Journal of Cell Science, vol. 112, 1999, pp. 2511-2520.

Article—*The $\alpha 4(IV)$ Chain of Basement Membrane Collagen*, Mariko Mariyama, Raghuram Kalluri, Billy G. Hudson, and Stephen T. Reeders, The Journal of Biological Chemistry, vol. 267, No. 2, Jan. 15, 1992, pp. 1253-1258.

Information on Laminin A from sdb.bio.purdue.edu, 3 pages.

Paper entitled "Basic Integrin Info", May 5, 1997, from integrins.hypermart.net, 3 pages.

Paper entitled "Perturbation of b1-integrin function alters the development of murine mammary gland" by Marina Glukhova, Jan. 1999, Institut Curie, France, from mammary.nih.gov, 3 pages.

Research Papers entitled "Integrin Receptor Activation in Breast Cancer", by David Rose, D.V.M., Ph.D. from cbcrp.org (3 pages).

Summary of Article—*Rather Rapid Genomic Prep*, Gene, vol. 87, 1987, pp. 262-272.

Kim et al., "Advances in Clinically Relevant Metastic Breast Cancer Models", *Journal of Korean Breast Cancer Society*, 2004: 7: 141-147.

Lacroix, et al., "Relevance of breast cencer cell lines as models for breast tumours: an update", *Breast Cancer Research and Treatment*, 2004, 83: 249-289.

Alghisi, et al., Vascular Integrins in Tumor Angiogenesis: Mediators and Therapeutic Targets:, *Endothelium*, 2006, 13:2, 113-135.

Redding, et al., "Clinging to life: cell to matrix adhesion and cell survival", *cancer and Metastasis Reviews*, 2005, 24: 425-439.

Pinske, "RGD peptides confer survival to hepatocytes via the $\beta 1$-integrin-ILK-pAkt pathway", *Journal of Hepatology*, 42 (2005), 87-93.

* cited by examiner

FIGURE 1A

Rattus norvegicus laminin-5 alpha 3 chain
Contains G1 thru G5 subdomains
Cloned as SacI blunt/XbaI fragment GAGCTCATTCGCAGGCCAGAGATGCTGCGAACAAGGTTGCAATTCCC*ATGAGGTTCAAT*
*GGTAAATCTGGTGTTGAAGTCCGTCTGCCAAATGACCTAGAAGACTTGAAGGGATACAC*
*GTCTCTGTCTTTGTTCCTCCAAAGACCAGACTTAAGAGAGAATGGAGGCACTGAGGACA*
*TGTTTGTAATGTACCTTGGAAACAAGGATGCCTCCAAGGACTACATCGGCATGGCGGTT*
*GTAGATGGCCAGCTGACGTGTGTCTACAACCTGGGGGACCGAGAAGCTGAAGTTCAGAT*
*CGATCAGGTCCTGACGGAGAGTGAGTCTCAGGAGGCAGTTATGGACCGGGTGAAGTTCC*
*AGAGAATATATCAATTTGCCAAGCTTAATTACACCAAAGAAGCCACGTCCAATAAACCC*
*AAAGCTCCCGCGGTCTACGACCTGGAGGGTGGCAGTAGCAACACGCTCCTTAATTTGGA*
*TCCCGAGGACGCTGTGTTTTATGTCGGAGGTTACCCACCGGATTTTGAACTTCCTAGCA*
*GACTGCGGTTCCCTCCATACAAAGGCTGTATCGAACTAGATGACCTCAATGAAAACGTT*
*CTAAGCTTGTACAATTTCAAGACAACTTTCAATCTCAACACCACGGAGGTGGAGCCTTG*
*TAGGAGGAGAAAGGAAGAGTCAGACAAAAATTACTTTGAAGGTACAGGCTATGCTCGCA*
*TCCCTACTCAACCAAATGCTCCCTTCCCAAACTTCATACAGACCATCCAGACTACTGTG*
*GACAGAGGTTTACTGTTCTTCGCAGAAAACCAGGATAACTTCATATCTCTGAACATAGA*
*AGATGGCAATCTCATGGTGAGATACAAACTAAATTCAGAGCCACCCAAAGAGAAGGGAA*
*TTCGAGACACCATCAACGATGGGAAAGATCATTCGATCTTAATCACAATTGGAAAACTA*
*CAAAAACGCATGTGGATAAATGTGAACGAACGCAGTGTACGAATCGAAGGGGAAATATT*
*TGATTTCAGCACATATTATTTGGGCGGAATTCCAATTGCAATCAGAGAAAGGTTTAACA*
*TCTCAACGCCTGCTTTCCAAGGCTGCATGAAGAATCTGAAGAAAACCAGTGGGGTTGTC*
*AGGTTGAATGATACTGTGGGTGTAACCAAGAAGTGCTCAGAAGACTGGAAGCTTGTGCG*
*AACCGCCTCGTTCTCCAGAGGAGGGCAGATGAGCTTTACAAACTTGGACGTGCCCTCGA*
*CTGACCGCTTCCAGCTCTCCTTTGGGTTTCAGACCTTTCAACCCAGTGGCACACTGCTC*
*AATCATCAGACGCGGACAAGCAGCCTGCTGGTCACCCTGGAAGATGGGCACATTGAGTT*
*GAGCACTAGGGACAGCAACATCCCAATTTTCAAGTCTCCAGGGACCTACATGGACGGTT*
*TACTGCATCATGTATCTGTAATAAGTGACACCTCAGGTCTCCGCCTTCTCATCGATGAC*
*CAGGTCCTGAGAAGGAACCAGAGGCTTCCTAGCTTCTCTAACGCCCAGCAGTCGCTCCG*
*CCTTGGAGGAGGTCATTTCGAGGGTTGTATCAGCAATGTTTTAGTCCAAAGGTTTTCAC*
*AGAGTCCAGAAGTCCTGGATCTGGCCAGTAAATCTACCAAGAAGGATGCATCCCTAGGA*
*GGCTGCAGTTTAAACAAGCCACCTTTTCTTATGTTGTTTAAAAGTCCCAAGAGATTTAA*
*CAAGGGCCGGATTTTCAATGTTAATCAGCTGATGCAAGATGCACCTCAGGCCACAAGGA*
*GCACAGAGGCTTGGCAAGATGGGAGGTCCTGCCTACCACCTCTGAACACCAAGGCCTCT*
*CACAGAGCCCTGCAGTTTGGAGACAGCCCCACCAGCCACTTGCTACTCAAGCTTCCCCA*
*GGAACTGCTGAAACCTAGGTCACAGTTTTCTTTAGACATACAGACAACTTCCCCCAAAG*
*GACTGGTGTTTTACGCAGGCACCAAGGACTCCTTCCTGGCTCTTTATGTCGCAGATGGC*
*CGTGTTGTCTTTGCTTTGGGGGCAGGAGGGAAGAAACTGAGACTCAGGAGCAAGGAGAG*
*ATACCATGACGGGAAGTGGCACACGGTGGTGTTCGGACTAAATGGAGGAAAGGCACGCC*
*TGGTTGTGGATGGGCTAAGGGCCCAGGAAGGCAGTTTGCCTGGAAATTCTACCATCAGC*
*CCCAGAGAACAGGTTTACCTAGGGTTGCCGCTATCAAGAAAGCCAAAGAGCCTACCCCA*
*GCACAGTTTTGTGGGGTGCCTGAGAGATTTCCAGTTGAACTCGAAACCCTGGATTCTC*
*CTTCTGCGAGGTTTGGGGTATCTCCCTGCTTGGGTGGCTCTTTAGAGAAAGGCATTTAT*
*TTCTCCCAAGGAGGAGGCCATGTGATCCTAGCCAATTCTGTGTCCTTGGGGCCAGAGCT*

FIGURE 1B

*TAAGCTCACTTTCAGCATTCGCCCACGGAGTCTCACTGGGGTCTTAATACACGTCGGAA*
*GTCAATCTGGACAGCGCTTAAGTGTGTACATGGAGGCAGGAAAGGTCACAACCTCTGTG*
*AGCAGTGATGCAGGAGGAAGTGTGACATCAATTACACCGAAGCAGTCTCTGTGTGATGG*
*ACAGTGGCACTCGGTGGCAGTCTCCATTAAACAGCGCATCCTGCATCTAGA*

```
  48 atgaggttcaatggtaaatctggtgttgaagtccgtctgccaaat
      M  R  F  N  G  K  S  G  V  E  V  R  L  P  N
  93 gacctagaagacttgaagggatacacgtctctgtctttgttcctc
      D  L  E  D  L  K  G  Y  T  S  L  S  L  F  L
 138 caaagaccagacttaagagagaatggaggcactgaggacatgttt
      Q  R  P  D  L  R  E  N  G  G  T  E  D  M  F
 183 gtaatgtaccttggaaacaaggatgcctccaaggactacatcggc
      V  M  Y  L  G  N  K  D  A  S  K  D  Y  I  G
 228 atggcggttgtagatggccagctgacgtgtgtctacaacctgggg
      M  A  V  V  D  G  Q  L  T  C  V  Y  N  L  G
 273 gaccgagaagctgaagttcagatcgatcaggtcctgacggagagt
      D  R  E  A  E  V  Q  I  D  Q  V  L  T  E  S
 318 gagtctcaggaggcagttatggaccgggtgaagttccagagaata
      E  S  Q  E  A  V  M  D  R  V  K  F  Q  R  I
 363 tatcaatttgccaagcttaattacaccaaagaagccacgtccaat
      Y  Q  F  A  K  L  N  Y  T  K  E  A  T  S  N
 408 aaacccaaagctcccgcggtctacgacctggagggtggcagtagc
      K  P  K  A  P  A  V  Y  D  L  E  G  G  S  S
 453 aacacgctccttaatttggatcccgaggacgctgtgttttatgtc
      N  T  L  L  N  L  D  P  E  D  A  V  F  Y  V
 498 ggaggttacccaccggattttgaacttcctagcagactgcggttc
      G  G  Y  P  P  D  F  E  L  P  S  R  L  R  F
 543 cctccatacaaaggctgtatcgaactagatgacctcaatgaaaac
      P  P  Y  K  G  C  I  E  L  D  D  L  N  E  N
 588 gttctaagcttgtacaatttcaagacaactttcaatctcaacacc
      V  L  S  L  Y  N  F  K  T  T  F  N  L  N  T
 633 acggaggtggagccttgtaggaggagaaaggaagagtcagacaaa
      T  E  V  E  P  C  R  R  R  K  E  E  S  D  K
 678 aattactttgaaggtacaggctatgctcgcatccctactcaacca
      N  Y  F  E  G  T  G  Y  A  R  I  P  T  Q  P
 723 aatgctcccttcccaaacttcatacagaccatccagactactgtg
      N  A  P  F  P  N  F  I  Q  T  I  Q  T  T  V
 768 gacagaggtttactgttcttcgcagaaaaccaggataacttcata
      D  R  G  L  L  F  F  A  E  N  Q  D  N  F  I
 813 tctctgaacatagaagatggcaatctcatggtgagatacaaacta
      S  L  N  I  E  D  G  N  L  M  V  R  Y  K  L
 858 aattcagagccacccaaagagaagggaattcgagacaccatcaac
      N  S  E  P  P  K  E  K  G  I  R  D  T  I  N
 903 gatgggaagatcattcgatcttaatcacaattggaaaactacaa
      D  G  K  D  H  S  I  L  I  T  I  G  K  L  Q
 948 aaacgcatgtggataaatgtgaacgaacgcagtgtacgaatcgaa
      K  R  M  W  I  N  V  N  E  R  S  V  R  I  E
 993 ggggaaatattcgatttcagcacatattatttgggcggaattcca
      G  E  I  F  D  F  S  T  Y  Y  L  G  G  I  P
1038 attgcaatcagagaaaggttaacatctcaacgcctgctttccaa
      I  A  I  R  E  R  F  N  I  S  T  P  A  F  Q
1083 ggctgcatgaagaatctgaagaaaaccagtggggttgtcaggttg
      G  C  M  K  N  L  K  K  T  S  G  V  V  R  L
```

FIGURE 1C

```
1128 aatgatactgtgggtgtaaccaagaagtgctcagaagactggaag
      N  D  T  V  G  V  T  K  K  C  S  E  D  W  K
1173 cttgtgcgaaccgcctcgttctccagaggagggcagatgagcttt
      L  V  R  T  A  S  F  S  R  G  G  Q  M  S  F
1218 acaaacttggacgtgccctcgactgaccgcttccagctctccttt
      T  N  L  D  V  P  S  T  D  R  F  Q  L  S  F
1263 gggtttcagacctttcaaccagtggcacactgctcaatcatcag
      G  F  Q  T  F  Q  P  S  G  T  L  L  N  H  Q
1308 acgcggacaagcagcctgctggtcaccctggaagatgggcacatt
      T  R  T  S  S  L  L  V  T  L  E  D  G  H  I
1353 gagttgagcactagggacagcaacatcccaattttcaagtctcca
      E  L  S  T  R  D  S  N  I  P  I  F  K  S  P
1398 gggacctacatggacggtttactgcatcatgtatctgtaataagt
      G  T  Y  M  D  G  L  L  H  H  V  S  V  I  S
1443 gacacctcaggtctccgccttctcatcgatgaccaggtcctgaga
      D  T  S  G  L  R  L  L  I  D  D  Q  V  L  R
1488 aggaaccagaggcttcctagcttctctaacgcccagcagtcgctc
      R  N  Q  R  L  P  S  F  S  N  A  Q  Q  S  L
1533 cgccttggaggaggtcatttcgagggttgtatcagcaatgtttta
      R  L  G  G  G  H  F  E  G  C  I  S  N  V  L
1578 gtccaaaggttttcacagagtccagaagtcctggatctggccagt
      V  Q  R  F  S  Q  S  P  E  V  L  D  L  A  S
1623 aaatctaccaagaaggatgcatccctaggaggctgcagtttaaac
      K  S  T  K  K  D  A  S  L  G  G  C  S  L  N
1668 aagccaccttttcttatgttgtttaaaagtcccaagagatttaac
      K  P  P  F  L  M  L  F  K  S  P  K  R  F  N
1713 aagggccggatttcaatgttaatcagctgatgcaagatgcacct
      K  G  R  I  F  N  V  N  Q  L  M  Q  D  A  P
1758 caggccacaaggagcacagaggcttggcaagatggggaggtcctgc
      Q  A  T  R  S  T  E  A  W  D  G  R  S  C
1803 ctaccacctctgaacaccaaggcctctcacagagccctgcagttt
      L  P  P  L  N  T  K  A  S  H  R  A  L  Q  F
1848 ggagacagccccaccagccacttgctactcaagcttccccaggaa
      G  D  S  P  T  S  H  L  L  L  K  L  P  Q  E
1893 ctgctgaaacctaggtcacagttttctttagacatacagacaact
      L  L  K  P  R  S  Q  F  S  L  D  I  Q  T  T
1938 tccccaaaggactggtgttttacgcaggcaccaaggactccttc
      S  P  K  G  L  V  F  Y  A  G  T  K  D  S  F
1983 ctggctctttatgtcgcagatggccgtgttgtctttgctttgggg
      L  A  L  Y  V  A  D  G  R  V  V  F  A  L  G
2028 gcaggagggaagaaactgagactcaggagcaaggagagataccat
      A  G  G  K  K  L  R  L  R  S  K  E  R  Y  H
2073 gacgggaagtggcacacggtggtgttcggactaaatggaggaaag
      D  G  K  W  H  T  V  V  F  G  L  N  G  G  K
2118 gcacgcctggttgtggatgggctaagggcccaggaaggcagtttg
      A  R  L  V  V  D  G  L  R  A  Q  E  G  S  L
2163 cctggaaattctaccatcagccccagagaacaggtttacctaggg
      P  G  N  S  T  I  S  P  R  E  Q  V  Y  L  G
2208 ttgccgctatcaagaaagccaaagagcctaccccagcacagtttt
      L  P  L  S  R  K  P  K  S  L  P  Q  H  S  F
2253 gtggggtgcctgagagatttccagttgaactcgaaacccctggat
      V  G  C  L  R  D  F  Q  L  N  S  K  P  L  D
2298 tctccttctgcgaggtttggggtatctccctgcttgggtggctct
      S  P  S  A  R  F  G  V  S  P  C  L  G  G  S
```

FIGURE 1D

```
2343 ttagagaaaggcatttatttctcccaaggaggaggccatgtgatc
      L   E   K   G   I   Y   F   S   Q   G   G   G   H   V   I
2388 ctagccaattctgtgtccttggggccagagcttaagctcactttc
      L   A   N   S   V   L   G   P   E   L   K   L   T   F
2433 agcattcgcccacggagtctcactggggtcttaatacacgtcgga
      S   I   R   P   R   S   L   T   G   V   L   I   H   V   G
2478 agtcaatctggacagcgcttaagtgtgtacatggaggcaggaaag
      S   Q   S   G   Q   R   L   S   V   Y   M   E   A   G   K
2523 gtcacaacctctgtgagcagtgatgcaggaggaagtgtgacatca
      V   T   T   S   V   S   S   D   A   G   G   S   V   T   S
2568 attacaccgaagcagtctctgtgtgatggacagtggcactcggtg
      I   T   P   K   Q   S   L   C   D   G   Q   W   H   S   V
2613 gcagtctccattaaacagcgcatcctgcatctaga 2647
      A   V   S   I   K   Q   R   I   L   H   L
```

FIGURE 2A

Rattus norvegicus laminin-5 alpha 3 chain
Contains G1 thru G3 subdomains
Cloned as PvuII/XbaI blunt fragment GAGCTCATTCAGCAGGCCAGAGATGCTGCGAACAAGGTTGCAATTCCC*ATGAGGTTCAA*
*TGGTAAATCTGGTGTTGAAGTCCGTCTGCCAAATGACCTAGAAGACTTGAAGGGATACA*
*CGTCTCTGTCTTTGTTCCTCCAAAGACCAGACTTAAGAGAGAATGGAGGCACTGAGGAC*
*ATGTTTGTAATGTACCTTGGAAACAAGGATGCCTCCAAGGACTACATCGGCATGGCGGT*
*TGTAGATGGCCAGCTGACGTGTGTCTACAACCTGGGGGACCGAGAAGCTGAAGTTCAGA*
*TCGATCAGGTCCTGACGGAGAGTGAGTCTCAGGAGGCAGTTATGGACCGGGTGAAGTTC*
*CAGAGAATATATCAATTTGCCAAGCTTAATTACACCAAAGAAGCCACGTCCAATAAACC*
*CAAAGCTCCCGCGGTCTACGACCTGGAGGGTGGCAGTAGCAACACGCTCCTTAATTTGG*
*ATCCCGAGGACGCTGTGTTTTATGTCGGAGGTTACCCACCGGATTTTGAACTTCCTAGC*
*AGACTGCGGTTCCCTCCATACAAAGGCTGTATCGAACTAGATGACCTCAATGAAAACGT*
*TCTAAGCTTGTACAATTTCAAGACAACTTTCAATCTCAACACCACGGAGGTGGAGCCTT*
*GTAGGAGGAGAAAGGAAGAGTCAGACAAAAATTACTTTGAAGGTACAGGCTATGCTCGC*
*ATCCCTACTCAACCAAATGCTCCCTTCCCAAACTTCATACAGACCATCCAGACTACTGT*
*GGACAGAGGTTTACTGTTCTTCGCAGAAAACCAGGATAACTTCATATCTCTGAACATAG*
*AAGATGGCAATCTCATGGTGAGATACAAACTAAATTCAGAGCCACCCAAAGAGAAGGGA*
*ATTCGAGACACCATCAACGATGGGAAAGATCATTCGATCTTAATCACAATTGGAAAACT*
*ACAAAAACGCATGTGGATAAATGTGAACGAACGCAGTGTACGAATCGAAGGGGAAATAT*
*TTGATTTCAGCACATATTATTTGGGCGGAATTCCAATTGCAATCAGAGAAAGGTTTAAC*
*ATCTCAACGCCTGCTTTCCAAGGCTGCATGAAGAATCTGAAGAAAACCAGTGGGGTTGT*
*CAGGTTGAATGATACTGTGGGTGTAACCAAGAAGTGCTCAGAAGACTGGAAGCTTGTGC*
*GAACCGCCTCGTTCTCCAGAGGAGGGCAGATGAGCTTTACAAACTTGGACGTGCCCTCG*
*ACTGACCGCTTCCAGCTCTCCTTTGGGTTTCAGACCTTTCAACCCAGTGGCACACTGCT*
*CAATCATCAGACGCGGACAAGCAGCCTGCTGGTCACCCTGGAAGATGGGCACATTGAGT*
*TGAGCACTAGGGACAGCAACATCCCAATTTTCAAGTCTCCAGGGACCTACATGGACGGT*
*TTACTGCATCATGTATCTGTAATAAGTGACACCTCAGGTCTCCGCCTTCTCATCGATGA*
*CCAGGTCCTGAGAAGGAACCAGAGGCTTCCTAGCTTCTCTAACGCCCAGCAGTCGCTCC*
*GCCTTGGAGGAGGTCATTTCGAGGGTTGTATCAGCAATGTTTTAGTCCAAAGGTTTTCA*
*CAGAGTCCAGAAGTCCTGGATCTGGCCAGTAAATCTACCAAGAAGGATGCATCCCTAGG*
*AGGCTGCAGTTTAAACAAGCCACCTTTTCTTATGTTGTTTAAAAGTCCCAAGAGATTTA*
*ACAAGGGCCGGATTTTCAATGTTAATCAGCTG*

```
 49 atgaggttcaatggtaaatctggtgttgaagtccgtctgccaaat
      M  R  F  N  G  K  S  G  V  E  V  R  L  P  N
 94 gacctagaagacttgaagggatacacgtctctgtctttgttcctc
      D  L  E  D  L  K  G  Y  T  S  L  S  L  F  L
139 caaagaccagacttaagagagaatggaggcactgaggacatgttt
      Q  R  P  D  L  R  E  N  G  G  T  E  D  M  F
184 gtaatgtaccttggaaacaaggatgcctccaaggactacatcggc
      V  M  Y  L  G  N  K  D  A  S  K  D  Y  I  G
229 atggcggttgtagatggccagctgacgtgtgtctacaacctgggg
      M  A  V  V  D  G  Q  L  T  C  V  Y  N  L  G
```

FIGURE 2B

```
 274 gaccgagaagctgaagttcagatcgatcaggtcctgacggagagt
      D  R  E  A  E  V  Q  I  D  Q  V  L  T  E  S
 319 gagtctcaggaggcagttatggaccgggtgaagttccagagaata
      E  S  Q  E  A  V  M  D  R  V  K  F  Q  R  I
 364 tatcaatttgccaagcttaattacaccaaagaagccacgtccaat
      Y  Q  F  A  K  L  N  Y  T  K  E  A  T  S  N
 409 aaacccaaagctcccgcggtctacgacctggagggtggcagtagc
      K  P  K  A  P  A  V  Y  D  L  E  G  G  S  S
 454 aacacgctccttaatttggatcccgaggacgctgtgttttatgtc
      N  T  L  L  N  L  D  P  E  D  A  V  F  Y  V
 499 ggaggttacccaccggatttt gaacttcctagcagactgcggttc
      G  G  Y  P  P  D  F  E  L  P  S  R  L  R  F
 544 cctccatacaaaggctgtatcgaactagatgacctcaatgaaaac
      P  P  Y  K  G  C  I  E  L  D  D  L  N  E  N
 589 gttctaagcttgtacaatttcaagacaactttcaatctcaacacc
      V  L  S  L  Y  N  F  K  T  T  F  N  L  N  T
 634 acggaggtggagccttgtaggaggagaaaggaagagtcagacaaa
      T  E  V  E  P  C  R  R  R  K  E  E  S  D  K
 679 aattactttgaaggtacaggctatgctcgcatccctactcaacca
      N  Y  F  E  G  T  G  Y  A  R  I  P  T  Q  P
 724 aatgctcccttcccaaacttcatacagaccatccagactactgtg
      N  A  P  F  P  N  F  I  Q  T  I  Q  T  T  V
 769 gacagaggtttactgttcttcgcagaaaaccaggataacttcata
      D  R  G  L  L  F  F  A  E  N  Q  D  N  F  I
 814 tctctgaacatagaagatggcaatctcatggtgagatacaaacta
      S  L  N  I  E  D  G  N  L  M  V  R  Y  K  L
 859 aattcagagccacccaaagagaagggaattcgagacaccatcaac
      N  S  E  P  P  K  E  K  G  I  R  D  T  I  N
 904 gatgggaaagatcattcgatcttaatcacaattggaaaactacaa
      D  G  K  D  H  S  I  L  I  T  I  G  K  L  Q
 949 aaacgcatgtggataaatgtgaacgaacgcagtgtacgaatcgaa
      K  R  M  W  I  N  V  N  E  R  S  V  R  I  E
 994 ggggaaatatttgatttcagcacatattatttgggcggaattcca
      G  E  I  F  D  F  S  T  Y  Y  L  G  G  I  P
1039 attgcaatcagagaaaggtttaacatctcaacgcctgctttccaa
      I  A  I  R  E  R  F  N  I  S  T  P  A  F  Q
1084 ggctgcatgaagaatctgaagaaaaccagtggggttgtcaggttg
      G  C  M  K  N  L  K  K  T  S  G  V  V  R  L
1129 aatgatactgtgggtgtaaccaagaagtgctcagaagactggaag
      N  D  T  V  G  V  T  K  K  C  S  E  D  W  K
1174 cttgtgcgaaccgcctcgttctccagaggagggcagatgagcttt
      L  V  R  T  A  S  F  S  R  G  G  Q  M  S  F
1219 acaaacttggacgtgccctcgactgaccgcttccagctctccttt
      T  N  L  D  V  P  S  T  D  R  F  Q  L  S  F
1264 gggtttcagacctttcaacccagtggcacactgctcaatcatcag
      G  F  Q  T  F  Q  P  S  G  T  L  L  N  H  Q
1309 acgcggacaagcagcctgctggtcaccctggaagatgggcacatt
      T  R  T  S  S  L  L  V  T  L  E  D  G  H  I
1354 gagttgagcactagggacagcaacatcccaattttcaagtctcca
      E  L  S  T  R  D  S  N  I  P  I  F  K  S  P
1399 gggacctacatggacggtttactgcatcatgtatctgtaataagt
      G  T  Y  M  D  G  L  L  H  H  V  S  V  I  S
1444 gacaccctcaggtctccgccttctcatcgatgaccaggtcctgaga
      D  T  S  G  L  R  L  L  I  D  D  Q  V  L  R
```

FIGURE 2C

```
1489 aggaaccagaggcttcctagcttctctaacgcccagcagtcgctc
      R  N  Q  R  L  P  S  F  S  N  A  Q  Q  S  L
1534 cgccttggaggaggtcatttcgagggttgtatcagcaatgtttta
      R  L  G  G  H  F  E  G  C  I  S  N  V  L
1579 gtccaaaggttttcacagagtccagaagtcctggatctggccagt
      V  Q  R  F  S  Q  S  P  E  V  L  D  L  A  S
1624 aaatctaccaagaaggatgcatccctaggaggctgcagtttaaac
      K  S  T  K  K  D  A  S  L  G  G  C  S  L  N
1669 aagccaccttttcttatgttgtttaaaagtcccaagagatttaac
      K  P  P  F  L  M  L  F  K  S  P  K  R  F  N
1714 aagggccggatttttcaatgttaatcagctg 1743
      K  G  R  I  F  N  V  N  Q  L
```

FIGURE 3

Rattus norvegicus laminin-5 alpha 3 chain
Contains G3 subdomain
Cloned as EcoRI/PvuII blunt fragment GAATTCCAATTGCAATCAGAGAAAGGTTTAACATCTCAACGCCTGCTTTCCAAGGCTGC*ATG*
*AAGAATCTGAAGAAAACCAGTGGGGTTGTCAGGTTGAATGATACTGTGGGTGTAACCAAGAA*
*GTGCTCAGAAGACTGGAAGCTTGTGCGAACCGCCTCGTTCTCCAGAGGAGGGCAGATGAGCT*
*TTACAAACTTGGACGTGCCCTCGACTGACCGCTTCCAGCTCTCCTTTGGGTTTCAGACCTTT*
*CAACCCAGTGGCACACTGCTCAATCATCAGACGCGGACAAGCAGCCTGCTGGTCACCCTGGA*
*AGATGGGCACATTGAGTTGAGCACTAGGGACAGCAACATCCCAATTTTCAAGTCTCCAGGGA*
*CCTACATGGACGGTTTACTGCATCATGTATCTGTAATAAGTGACACCTCAGGTCTCCGCCTT*
*CTCATCGATGACCAGGTCCTGAGAAGGAACCAGAGGCTTCCTAGCTTCTCTAACGCCCAGCA*
*GTCGCTCCGCCTTGGAGGAGGTCATTTCGAGGGTTGTATCAGCAATGTTTTAGTCCAAAGGT*
*TTTCACAGAGTCCAGAAGTCCTGGATCTGGCCAGTAAATCTACCAAGAAGGATGCATCCCTA*
*GGAGGCTGCAGTTTAAACAAGCCACCTTTTCTTATGTTGTTTAAAAGTCCCAAGAGATTTAA*
*CAAGGGCCGGATTTTCAATGTTAATCAGCTG*

```
 60 atgaagaatctgaagaaaaccagtggggttgtcaggttgaatgat
     M  K  N  L  K  K  T  S  G  V  V  R  L  N  D
105 actgtgggtgtaaccaagaagtgctcagaagactggaagcttgtg
     T  V  G  V  T  K  K  C  S  E  D  W  K  L  V
150 cgaaccgcctcgttctccagaggagggcagatgagctttacaaac
     R  T  A  S  F  S  R  G  G  Q  M  S  F  T  N
195 ttggacgtgccctcgactgaccgcttccagctctcctttgggttt
     L  D  V  P  S  T  D  R  F  Q  L  S  F  G  F
240 cagacctttcaacccagtggcacactgctcaatcatcagacgcgg
     Q  T  F  Q  P  S  G  T  L  L  N  H  Q  T  R
285 acaagcagcctgctggtcaccctggaagatgggcacattgagttg
     T  S  S  L  L  V  T  L  E  D  G  H  I  E  L
330 agcactagggacagcaacatcccaattttcaagtctccagggacc
     S  T  R  D  S  N  I  P  I  F  K  S  P  G  T
375 tacatggacggtttactgcatcatgtatctgtaataagtgacacc
     Y  M  D  G  L  L  H  H  V  S  V  I  S  D  T
420 tcaggtctccgccttctcatcgatgaccaggtcctgagaaggaac
     S  G  L  R  L  L  I  D  D  Q  V  L  R  R  N
465 cagaggcttcctagcttctctaacgcccagcagtcgctccgcctt
     Q  R  L  P  S  F  S  N  A  Q  Q  S  L  R  L
510 ggaggaggtcatttcgagggttgtatcagcaatgttttagtccaa
     G  G  G  H  F  E  G  C  I  S  N  V  L  V  Q
555 aggttttcacagagtccagaagtcctggatctggccagtaaatct
     R  F  S  Q  S  P  E  V  L  D  L  A  S  K  S
600 accaagaaggatgcatccctaggaggctgcagtttaaacaagcca
     T  K  D  A  S  L  G  G  C  S  L  N  K  P
645 ccttttcttatgttgtttaaaagtcccaagagatttaacaagggc
     P  F  L  M  L  F  K  S  P  K  R  F  N  K  G
690 cggattttcaatgttaatcagctg 713
     R  I  F  N  V  N  Q  L
```

Figure 5

Table 1. Cloning and expression vectors constructed for rat laminin 5-alpha 3 chain G Domains

| Name | vector | transformed | insert | cloning region | restriction digest | designed from |
|---|---|---|---|---|---|---|
| pHB1 | pGEM T-easy | E. coli GM2163 | 5C5 | 932-3242 bp | designed PCR primers | original cDNA fragment |
| pHB2 | pGEM T-easy | E. coli GM2163 | 3'alpha3 | 3092-5250 bp | designed PCR primers | original cDNA fragment |
| pHB3 | pYES2 | E. coli DH5alphaMCR | modified 3'alpha3 | 1761 bp fragment | XbaI/ EcoRI partial | pHB2 |
| pHB4 | pYES2 | E. coli DH5alphaMCR | G1-G5 | 822 bp fragment | SacI/ EcoRI | pHB1 |
| | | | | added to 3'alpha3 in vector | SacI/ EcoRI | pHB3 |
| pHB5 | does not exist | | modified 5C5 | | | |
| pHB6 | pPICZalphaB | P. pastoris SMD1168 | G1-G5 | 2364-4990 bp | SacI/ XbaI | pHB4 |
| pHB7 | pPICZalphaB | P. pastoris SMD1168 | G3-G5 | 3239-4990 bp | EcoRI/ XbaI | pHB6 |
| pHB8 | pPICZalphaB | P. pastoris SMD1168 | G1-G3 | 2364-4097 bp | PvuII/ XbaI' | pHB6 |
| pHB9 | pPICZalphaB | P. pastoris SMD1168 | G3 | 3386-4097 bp | EcoRI/ PvuII' | pHB7 |

INHIBITION OF PATHOGENIC AGENTS INCLUDING α6β1 INTEGRIN RECEPTOR OR α6β4 INTEGRIN RECEPTOR AT A SURFACE

CROSS REFERENCE TO RELATED APPLICATIONS

The present application is a continuation application of U.S. patent application Ser. No. 10/817,423 having a filing date of Apr. 2, 2004, now abandoned.

BACKGROUND OF THE INVENTION

While treatment of disease has progressed far in the last century, many current treatments leave much to be desired when considering the overall welfare of the patient. For instance, currently, chemotherapy and radiation treatment remain the most widely used forms of cancer treatment known. However, such treatments are generic in their attack on the patient's system, attacking both healthy as well as diseased tissues and systems.

Many pathogenic agents, such as cancer cells, for example, use naturally occurring cellular surface receptors, primarily integrins, not only to invade healthy tissue but also for motility within the host body, which, in the case of cancer, can lead to metastasis. Integrins are part of a large family of cell adhesion receptors that are involved in cell/extracellular matrix as well as cell/cell interaction. Integrins are the main method that cells utilize to bind to and respond to the extracellular matrix. Functionally, integrin receptors are composed of two transmembrane glycoprotein subunits, an α subunit and a β subunit. Presently, 16α and 8β subunits have been identified.

Pathogens which contain and utilize integrin receptors for interaction with the extracellular matrix or cells of a host can exhibit highly efficient invasion of and motility within an organism due to the nature of the integrin/ligand interactions. Specifically, individual integrin receptors bind their ligands with low affinity (on the order of $10^{-6}$ to $10^{-9}$ liters/mole), however, they also exist on cell surfaces in very high concentration, generally 10 to 100 times greater than other types of cell-surface receptors. Following suitable stimulation, integrins on a cell surface will cluster and form hemidesmosomes which can provide a focal contact for adhesion. The combined weak affinities of the multiple integrins at the focal contact can give rise to a spot on the cell surface with suitable adhesive capacity to form an adherence to the ligand. This binding motif provides a method for a single integrin-containing cell to bind simultaneously but weakly to a large number of matrix molecules while still maintaining the ability to explore the cellular environment. The low affinity integrin/ligand binding motif thus provides an efficient route for integrin-containing pathogens to bind to and invade healthy cells while still maintaining cell motility for further invasion.

What is needed in the art are novel treatment methods for disease that can specifically target the pathogens of the disease. Specifically, what is needed in the art are treatment methods that can interfere with the binding processes of the pathogens and prevent initial invasion of healthy cells and motility of the pathogens within the body. Additionally, what is needed in the art is a method to specifically target and bind pathogens with disease fighting agents, such as chemotherapy agents, while not grossly interfering with the healthy systems and tissue that the disease has not yet affected.

SUMMARY OF THE INVENTION

According to one embodiment of the present invention, a therapeutic composition for treatment of disease is disclosed. The therapeutic composition can include a polypeptide capable of binding to at least one of α6β1 integrin receptor and α6β4 integrin receptor, wherein the polypeptide comprises the G domain of the laminin-5 α3 chain or a fragment, mutant, homolog, ortholog, analog, or allele thereof. The therapeutic composition also includes a pharmaceutically compatible carrier for the polypeptide.

In one particular embodiment, the polypeptides of the present invention can comprise the polypeptide as disclosed in SEQ ID NO:2, or a fragment, mutant, homolog, ortholog, analog, or allele thereof. Optionally, the polypeptides of the present invention can comprise the polypeptide as disclosed in SEQ ID NO:4 or SEQ ID NO: 6 or fragments, mutants, homologs, orthologs, analogs, or alleles of such. In one embodiment, the polypeptide can have at least 70% sequence identity with the reference sequence, i.e., SEQ ID NO:2, SEQ ID NO:4, or SEQ ID NO:6.

The therapeutic composition of the present invention can be in any suitable form. For instance, the composition can be a solid or a liquid composition. In various embodiments, the pharmaceutically compatible carrier can include a gelatin, water, an oil, or a sustained release matrix.

The compositions of the present invention can also include other therapeutic agents, in addition to the disclosed polypeptides. For instance, the compositions can include one or more chemotherapeutic agents or radioactive agents for treatment of a disease, such as a cancer.

In one embodiment, the therapeutic agent of the present invention can be a fused or chimeric polypeptide agent. According to this embodiment, the therapeutic agent can include a first component comprising a polypeptide capable of binding to at least one of α6β1 integrin receptor and α6β4 integrin receptor, wherein the polypeptide comprises the G domain of the laminin-5 α3 chain or a fragment, mutant, homolog, ortholog, analog, or allele thereof. The agent can also include a second component that is chemically bound to the first component. The second component can be any agent for use in the treatment of the disease. For instance, the second component can contribute to the destruction or neutralization of the pathogen bound by the polypeptides of the invention.

The second component can be a protein or a non-protein agent, as desired. For example, the second component can be cytokines, whole antibodies or fractions thereof, cell-surface receptors, ligands for cell-surface receptors, or any suitable organic molecules.

The disclosed invention is also directed to the nucleotide sequences that encode the therapeutic agents. In one particular embodiment, the disclosed invention is directed to an isolated polynucleotide including a first nucleotide sequence encoding the disclosed polypeptides and a second nucleotide sequence that encodes a polypeptide for use in the destruction or neutralization of the pathogens that can be bound by the polypeptides of the invention.

In various embodiments, the first nucleotide sequence can have at least about 70% sequence identity with SEQ ID NO:1, SEQ ID NO:3, or SEQ ID NO: 5.

The isolated polynucleotide can, in one embodiment be operably linked to an expression control sequence.

The invention is also directed to a host cell transformed with the disclosed polynucleotides. A host cell can be, for example, a bacterial, yeast, mammalian, insect, or plant cell.

The present invention is also directed to methods of treating a disease, such as, for example, breast cancer, with the disclosed therapeutic agents. In general, the methods include contacting a pathogen that includes α6β1 integrin receptors and/or α6β4 integrin receptors on the surface thereof with the therapeutic agents as herein described. Upon contact, the therapeutic agents can then bind to the pathogen.

For example, the method can be carried out in vivo and the therapeutic agent can contact the pathogen via a suitable pharmaceutically acceptable administration system. The binding of the agent to the pathogen can mask the integrin receptors of the pathogen and thus prevent the pathogen from binding to the extracellular matrix of the host. In certain embodiments, the method can also include the delivery of a second component of the therapeutic agent to the pathogen, the second component aiding in the destruction or neutralization of the pathogen.

Pharmaceutically acceptable administration systems can include, for example, parenteral systems, oral systems, and sustained release systems.

BRIEF DESCRIPTION OF THE FIGURES

A full and enabling disclosure of the present invention, including the best mode thereof, to one of ordinary skill in the art, is set forth more particularly in the remainder of the specification, including reference to the accompanying figures, in which:

FIGS. 1A-1D depict the nucleotide (SEQ ID NO: 1) and the amino acid (SEQ ID NO: 2) sequences of the complete globular domain G-1 to G-5 of the *Rattus norvegicus* laminin-5 α3 chain;

FIGS. 2A-2C depict the nucleotide (SEQ ID NO: 3) and the amino acid (SEQ ID NO: 4) sequences of the globular subdomains G-1 through G-3 of the *Rattus norvegicus* laminin-5 α3 chain;

FIG. 3 depicts the nucleotide (SEQ ID NO: 5) and the amino acid (SEQ ID NO: 6) sequences of the G-3 subdomain of the *Rattus norvegicus* laminin-5 α3 chain;

FIG. 5 is a table depicting cloning and expression vectors constructed and utilized in Example 1.

Definitions of Terms

Figure 4:
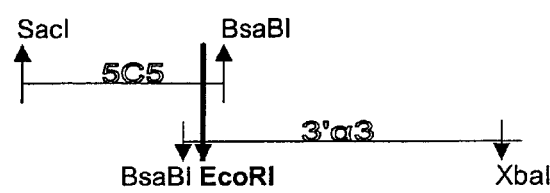
FIG. 4 depicts a restriction map for plasmid 5C5 and plasmid 3'α3 utilized in the Examples.

"Polypeptide" is herein defined to indicate a molecular chain of amino acids and does not refer to a specific length of the product. Thus, peptides, oligopeptides and proteins are included within the definition of polypeptide. This term is also intended to include polypeptides that have been subjected to post-expression modifications such as, for example, glycosylations, acetylations, phosphorylations and the like.

For purposes of this disclosure, the term "protein" is herein defined to include any molecular chain of amino acids that is capable of interacting structurally, enzymatically or otherwise with other proteins, polypeptides or any other organic or inorganic molecule.

The term "fragment" in reference to a protein or polypeptide is herein defined as an amino acid sequence of that protein that is shorter than the entire protein, but comprising at least about 25 consecutive amino acids of the full polypeptide.

For purposes of this disclosure, an "ortholog" is herein defined to be a nucleotide or polypeptide sequence with similar function to a nucleotide or polypeptide sequence in an evolutionarily related species. Loci in two species are said to be "orthologous" when they have arisen from the same locus of their common ancestor. Orthologous polynucleotide sequences exist at loci in different species that are sufficiently similar to each other in their nucleotide sequences to suggest that they originated from a common ancestral sequence. Orthologous sequences arise when a lineage splits into two species, rather than when a sequence is duplicated within a genome. Proteins that are orthologs of each other are encoded by genes of two different species, and the genes are said to be orthologous.

The term "mutant" is herein defined to be a polypeptide that includes any change in the amino acid sequence relative to the amino acid sequence of the reference polypeptide. Such changes can arise either spontaneously or by manipulations including those chemical derivatives brought about by chemical energy (e.g., X-ray), other forms of chemical mutagenesis, by genetic engineering, or as a result of mating or other forms of exchange of genetic information. Mutations include, e.g., base changes, deletions, insertions, inversions, translocations, or duplications. Mutants may or may not also comprise additional amino acids derived from the process of cloning, e.g., amino acid residues or amino acid sequences corresponding to full or partial linker sequences. Mutants/fragments of the polypeptides of the present invention can also be generated by PCR cloning, or by *Pseudomonas* elastase digestion, as described by Mariyama, M. et al. (1992, J. Biol. Chem. 267:1253-1258).

The term "homolog" is herein defined to describe two nucleotide or polypeptide sequences that differ from each other by substitutions that do not effect the overall functioning of the polypeptide. For example, when considering polypeptide sequences, homologs include polypeptides having substitution of one amino acid at a given position in the sequence for another amino acid of the same class (e.g., amino acids that share characteristics of hydrophobicity, charge, pK or other conformational or chemical properties, e.g., valine for leucine, arginine for lysine). Homologs also include polypeptides and nucleotide sequences including one or more substitutions, deletions, or insertions, located at positions of the sequence that do not alter the conformation or folding of the polypeptide to the extent that the biological activity of the polypeptide is destroyed. Examples of possible homologs include polypeptide sequences including substitution of one non-polar (hydrophobic) residue such as isoleucine, valine, leucine or methionine for one another; the substitution of one polar (hydrophilic) residue for another such as between arginine and lysine, between glutamine and asparagine, or between threonine and serine; the substitution of one basic residue such as lysine, arginine or histidine for another; the substitution of one acidic residue, such as aspartic acid or glutamic acid for the another; or the use of a chemically derivatized residue in place of a non-derivatized residue, as long as the homolog polypeptide displays substantially similar biological activity to the reference polypeptide, and in particular the ability to be recognized and be bound by $\alpha 6\beta 1$ and/or $\alpha 6\beta 4$ integrin receptors.

The term "analog" is herein defined to be a non-natural molecule substantially similar to either the entire reference protein or polypeptide, or a fragment or allelic variant thereof, and having substantially the same or superior biological activity. The term "analog" is intended to include derivatives (e.g., chemical derivatives, as defined above) of the biologically active polypeptide, as well as its fragments, mutants, homologs, orthologs, and allelic variants, which derivatives exhibit a qualitatively similar agonist or antagonist effect to that of the unmodified polypeptide.

The term "allele" of a polypeptide is herein defined to be a polypeptide sequence containing a naturally-occurring sequence variation relative to the polypeptide sequence of the reference polypeptide. Similarly, an allele of a polynucleotide encoding the polypeptide is herein defined to be a polynucleotide containing a sequence variation relative to the reference polynucleotide sequence encoding the reference polypeptide, where the allele of the polynucleotide encoding the polypeptide encodes an allelic form of the polypeptide.

"Operably linked" refers to a situation wherein the components described are in a relationship permitting them to function in their intended manner. For instance, a control sequence "operably linked" to a coding sequence is ligated in such a manner that expression of the coding sequence is achieved under conditions compatible with the control sequence. A "coding sequence" is a polynucleotide sequence which is transcribed into mRNA and translated into a polypeptide when placed under the control of (e.g., operably linked to) appropriate regulatory sequences. The boundaries of the coding sequence are determined by a translation start codon at the 5'-terminus and a translation stop codon at the 3'-terminus. Such boundaries can be naturally-occurring, or can be introduced into or added to the polynucleotide sequence by methods known in the art. A coding sequence can include, but is not limited to, genomic DNA, mRNA, cDNA, and recombinant polynucleotide sequences.

The term "sequence identity," as used herein, refers to the subunit sequence similarity between two polymeric molecules. For example, the sequence similarity between two polynucleotides or two polypeptides. When a subunit position in both of the two molecules is occupied by the same monomeric subunit, then they are identical at that position. The identity between two sequences is a direct function of the number of matching or identical positions. For example, if half of the positions in two peptide or compound sequences are identical, then the two sequences are 50% identical. The identity between two sequences is a direct function of the number of matching or identical positions. Thus, if a portion of the reference sequence is deleted in a particular peptide, that deleted section is not counted for purposes of calculating sequence identity. For example, when comparing a first polymer including monomers $R_1R_2R_3R_4R_5R_6$ with another polymer including monomers $R_1R_2R_3R_4R_6$, the two polymers have 5 out of 6 positions in common, and therefore would be described as sharing 83.3% sequence identity.

The term "pathogen" is herein defined to include any disease causing agent. Pathogens can include disease causing agents that can infect a host from an external source, such as bacteria, fungus, virus, and the like, as well as pathogenic agents arising within the carrier of the disease, including abnormal cells such as cancer cells.

DETAILED DESCRIPTION OF THE INVENTION

Reference will now be made in detail to various embodiments of the invention, one or more examples of which are set forth below. Each embodiment is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used in another embodiment to yield a still further embodiment. Thus, it is intended that the present invention cover such modifications and variations as come within the scope of the appended claims and their equivalents.

The present invention is generally directed to a novel immunotherapy in which a protein or polypeptide agent is produced that is capable of binding to the surface receptors of a pathogen. Through this binding, the agent can mask the receptors of the pathogen and prevent the binding of the pathogen to healthy host cells. In addition, through this binding, the agent can, in one particular embodiment, be utilized to carry and bind other materials to the pathogen that can encourage the destruction or neutralization of the pathogen. More specifically, the therapeutic agents of the present invention comprise at least a portion of a laminin-5 chain that can be utilized as an immunotherapeutic agent against pathogens that include $\alpha 6\beta 1$ and/or $\alpha 6\beta 4$ integrin receptors on the surface of the pathogen.

Laminin is one of a family of heterotrimer protein complexes formed from various combinations of different $\alpha$, $\beta$, and $\gamma$ subunit chains. Laminins in general can be found in the basement membranes of the extracellular matrix and interact with other matrix macromolecules to contribute to cell differentiation, movement and maintenance. Laminin-5, comprising an $\alpha 3$ chain, a $\beta 3$ chain, and a $\gamma 2$ chain, is a member of the laminin family that has been shown to function as an adhesion and migration component for certain cells. The terminal portion of the laminin-5 $\alpha 3$ chain, the G domain, is further subdivided into 5 sub-domains, G1, G2, G3, G4, and G5. The G subdomains of the laminin-5 $\alpha 3$ chain have been shown to be necessary for adherence of laminin-5 to cells which have certain receptor integrins on their cell surface, specifically, cells containing $\alpha 6\beta 1$ and/or $\alpha 6\beta 4$ integrin receptors on the cell surface.

The present invention is generally directed to recognition and utilization of the binding characteristics of the G-domain of the laminin-5 $\alpha 3$ chain. More specifically, according to the present invention, the entire laminin-5 $\alpha 3$ G-domain as well as significant portions of the laminin-5 $\alpha 3$ G-domain have been sequenced and expressed for utilization in novel immunotherapies targeting pathogens containing specific integrin receptors on the surface, specifically, those containing $\alpha 6\beta 1$ and/or $\alpha 6\beta 4$ integrin receptors on the surface.

In one embodiment, therapeutic compositions comprising polypeptides of the disclosed portions of the G domain of the laminin-5 $\alpha 3$ chain have been developed that can be utilized to target and bind to the α6β1 and/or α6β4 integrin receptors on the surface of a pathogen. The present invention is also directed to mutants, homologs, orthologs, analogs, and/or allelic variants of the laminin-5 α3 G domains disclosed herein possessing the ability to be recognized and bound by α6β1 and/or α6β4 integrin receptors.

The laminin-5 of the present invention can be obtained from a variety of sources. For example, while SEQ ID NO: 1-6 are particular to rat laminin-5 G domains (and in particular, *Rattus norvegicus*), other sources of laminin-5 are encompassed by the disclosed invention. Such sources include, but are not limited to mouse laminin-5, *Mus musculus* laminin-5, artificial laminin-5 and human laminin-5.

In one embodiment, therapeutic agents can be developed comprising that portion of the G-domain of the laminin-5 α3 chain that binds to α6β1 and/or α6β4 integrin receptors, which is understood to exist in the G-3 subdomain of the chain. For instance, in one embodiment, the therapeutic agents of the present invention can include polypeptides including all of the G1-G5 subdomains of the laminin-5 α3 chain as identified in SEQ ID NO: 2 as well as mutants, homologs, orthologs, analogs, and/or allelic variants of the laminin-5 α3 G1-G5 domain as identified in SEQ ID NO: 2.

In other embodiments, the therapeutic agents of the present invention can include only those sub-domains of the laminin-5 α3 chain believed to contain the specific amino acid sequences that bind to the α6β1 and/or α6β4 integrin receptors of the cellular pathogens. For instance, in one embodiment, the therapeutic agents of the present invention can include the G1-G3 subdomains of the laminin-5 α3 chain as identified in SEQ ID NO: 4 as well as mutants, homologs, orthologs, analogs, and/or allelic variants of the laminin-5 α3 G1-G3 subdomains as identified in SEQ ID NO: 4.

In another embodiment, the therapeutic agents of the present invention can include only the G3 subdomain of the laminin-5 α3 chain as identified in SEQ ID NO: 6 as well as mutants, homologs, orthologs, analogs, and/or allelic variants of the laminin-5 α3 G3 subdomain as identified in SEQ ID NO: 6.

Encompassed by the present invention are proteins and polypeptides that have substantially the same amino acid sequence as the laminin-5 α3 G domains as herein disclosed as well as the polynucleotides that encode such. By the term "substantially the same" is meant both the polypeptide and the polynucleotide that encodes such that can be recognized and bound by α6β1 and/or α6β4 integrin receptors. For example, in one embodiment, the nucleotide or amino acid sequence of the present invention can exhibit at least about 70% sequence identity with the reference sequence, at least about 80% sequence identity with the reference sequence, at least about 90% sequence identity, at least about 95% sequence identity, or at least about 97% sequence identity with the reference sequence. Optionally, the polypeptide can be only that small portion of the entire G domain that is recognized and bound by α6β1 and/or α6β4 integrin receptors.

In addition, the presently disclosed invention is directed not only to the disclosed polypeptides and the polynucleotides encoding such, but is also directed to the vectors and host cells containing such polynucleotides. Vectors encompassed by the disclosed invention include any molecules into which pieces of nucleic acid may be inserted or cloned that can transfer the nucleic acids carried thereby into a host cell. In some embodiments of the present invention, vectors may also bring about the replication and/or expression of the transferred nucleic acid pieces. An exemplary list of suitable vectors can include nucleic acid molecules derived from a plasmid, bacteriophage, or mammalian, plant or insect virus, or non-viral vectors such as ligand-nucleic acid conjugates, liposomes, or lipid-nucleic acid complexes.

In some embodiments of the present invention, the transferred nucleic acid molecule can be operatively linked to an expression control sequence to form an expression vector capable of expressing the transferred nucleic acid. Such transfer of nucleic acids is generally termed transformation, and refers to the insertion of an exogenous polynucleotide into a host cell, irrespective of the method used for the insertion. For example, direct uptake, transduction, electroporation, or f-mating, as are generally known in the art, can be utilized. The exogenous polynucleotide may be maintained as a non-integrated vector, for example, a plasmid, or alternatively, may be integrated into the host genome.

The vector into which the disclosed polynucleotides can be cloned may be chosen because it functions in either a prokaryotic organism, a eukaryotic organism, or both, as desired. An exemplary list of possible vectors include, for example, the pGEM™-T Easy vector, the pYES2 vector, the pPICZ.alpha series of vectors, the pET22b and pET28(a) vectors, and modified pPICZ.alpha series vectors.

Following the cloning of a polynucleotide into a suitable vector, the vector can be transformed into an appropriate host cell. By "host cell" is meant a cell which has been or can be used as the recipient of transferred nucleic acid by means of a vector. Host cells can be prokaryotic or eukaryotic, mammalian, plant, or insect, and can exist as single cells, or as a collection, e.g., as a culture, or in a tissue culture, or in a tissue or an organism. Host cells can also be derived from normal or diseased tissue from a multicellular organism, e.g., a mammal. Host cell, as used herein, is intended to include not only the original cell which was transformed with a nucleic acid, but also descendants of such a cell, which still contain the nucleic acid.

In one embodiment, isolated polynucleotides encoding the disclosed polypeptides can additionally comprise a polynucleotide linker encoding a peptide. Such linkers are generally known to those of skill in the art and can comprise, for example, at least one additional codon encoding at least one additional amino acid. Typically the linker comprises one to about twenty or thirty amino acids. The polynucleotide linker can be translated along with the disclosed polynucleotides resulting in the expression of the disclosed polypeptides with at least one additional amino acid residue at the amino or carboxyl terminus of the polypeptide. Importantly, the additional amino acid, or amino acids, do not compromise the recognition and binding capability of the polypeptides by α6β1 and/or α6β4 integrin receptors.

In one embodiment, following insertion of the disclosed polynucleotide into a vector, the vector can be transformed into an appropriate prokaryotic strain and the strain can be maintained under suitable culture conditions for the production of the encoded polypeptide.

In another embodiment of the present invention, a eukaryotic vector can be utilized that comprises a modified yeast vector. According to one particular embodiment, a plasmid can be utilized that contains a multiple cloning site. In addition, the multiple cloning site can have inserted thereto a His.Tag motif, as is generally known in the art. Optionally, the vector can be modified to add a restriction site, for example an NdeI site. Such sites are well known to those of skill in the art. Proteins and polypeptides produced according to this particular embodiment can comprise a histidine tag motif (His.tag) comprising one or more histidines, in one embodiment about 5-20 histidines. Of course, any tag should not interfere with the desired properties of the proteins and product, namely, the ability for recognition and binding thereto by α6β1 and/or α6β4 integrin receptors.

In one embodiment of the present invention, the disclosed polypeptides can be synthetically constructed amino acid sequences produced according to conventional methods of chemical synthesis as are generally known to those in the art.

Pathogens that can be targeted by the disclosed therapeutic agents can include any pathogens that include α6β1 and/or α6β4 integrin receptors on the surface. For example, in some embodiments, the disclosed therapeutic agents can be targeted toward certain cellular pathogens, including cancer cells, and specifically, breast cancer cells, prostate cancer cells, thyroid cancer cells, bladder cancer cells, colorectal cancer cells, intestinal cancer cells, squamous cell carcinomas, neuroblastomas, and fibrotic liver tissue cells.

In addition to the therapeutic agents herein disclosed, the present invention is also directed to methods for treatment of disease utilizing the disclosed therapeutic agents. For example, in one embodiment, the disclosed methods can be utilized for the destruction of primary and secondary cancer or tumor cells by contacting and binding the agents to the pathogenic cells and masking the integrin receptors of the cells, preventing communication between the pathogenic cells and the host and leading to the eventual death of the cancer cells.

In one particular embodiment, the present invention is directed to a method for the inhibition or elimination of metastatic cancer or tumor cells arising from primary tumor sites. According to this embodiment, the therapeutic agents of the present invention can be directed toward a tumor or cancer by use of any suitable pharmaceutically acceptable system and can contact the cancer cells in that targeted area. As the targeted cancer cells include α6β1 and/or α6β4 integrin receptors on the surface, the agents of the present invention can bind to the pathogens at the α6β1 and/or α6β4 integrin receptors. The binding of the therapeutic agents to the cellular pathogens can mask the receptors of the cancer cells, as discussed above, and motility of the metastatic cell can be prevented. In addition, in certain embodiments of the invention, this masking of the pathogen cannot only prevent the spread of the cancer, but can also destroy the cancerous cells, for example in those cases where the binding of the therapeutic agents to the cancer cells also prevents the cancer cells from obtaining necessary nutrition.

In other embodiments of the invention, treatment with the therapeutic agents can be combined with other known treatment agents or methods to destroy or treat a disease. More specifically, the polypeptides of the disclosed invention may be used in combination with themselves or other compositions and procedures for the treatment of diseases. For instance, in one embodiment, the disclosed polypeptides can be combined with another treatment agent such as a chemotherapeutic agent. For example, a therapeutic composition of the present invention can include the disclosed polypeptides and a second therapeutic agent such as Vasostatin or anti-alpha 6 integrin monoclonal antibodies with a pharmaceutically compatible carrier. In another embodiment, a disease may be treated conventionally with surgery, radiation, or chemotherapy, and the disclosed polypeptides may additionally be administered to the patient to further treat the disease such as by extension of the dormancy of micrometastases or to stabilize and inhibit the growth of any residual primary tumor.

In another embodiment, the disclosed polypeptides can be combined with other pharmaceutically acceptable excipients in forming therapeutic compositions. The compositions of the present invention may additionally contain other polypeptides or chemical compounds for disease treatment as are generally known in the art. Such additional factors and/or agents may be included in the composition to produce a synergistic effect with the polypeptides of the invention.

In one embodiment of the present invention, the disclosed polypeptides can be chemically combined with secondary materials so as to form a single agent comprising both materials. Generally, the second component of the combination agent can be useful in fighting the disease, for example can aid in destruction or neutralization of the pathogen. For example, in one embodiment, the recognition and binding of the polypeptides to the pathogen can be utilized as a method for delivering the second component directly to the pathogen. For example, the therapeutic agents of the present invention can include fusion polypeptides or chimeric polypeptides comprising the disclosed polypeptides of the laminin-5 α3 G domain, or their fragments, mutants, homologs, orthologs, analogs, and allelic variants, chemically combined with a secondary polypeptide material so as to form a single therapeutic agent. Exemplary secondary polypeptide materials can include, for example, IL-2, IL-3 IL-15, IL-12, IFN-γ, GM-CSF, CD40, CD40 ligand (CD40L), C3 Complement components, CD80, CD86, FAS, or FAS ligand (FASL). The nucleotide and amino acid sequences of each of these exemplary components are known in the art and can be found in the NBCI GenBank database.

In one embodiment, a fusion or chimeric product or polypeptide of the present invention can be produced as a result of recombinant expression and the cloning process as described above, and the polypeptide may be produced comprising additional amino acids or amino acid sequences corresponding to full or partial linker sequences. Alternatively, a fusion or chimeric product of the present invention can be a multimer of a single polypeptide. That is, a polypeptide including one or more repeating sequences of the disclosed polypeptides. In yet another embodiment, the therapeutic agents of the present invention can be fusion and chimeric polypeptides that can be formed of one or more of the different polypeptides as herein disclosed. For example, in one embodiment, a therapeutic agent according to the present invention can include a polypeptide comprising a polypeptide as disclosed according to SEQ ID NO: 2 in combination with one or more polypeptides as disclosed according to SEQ ID NO: 4 and/or SEQ ID NO: 6.

In yet another embodiment of the present invention, the therapeutic agent can be a fusion or chimeric product in which polypeptides as herein disclosed are chemically combined with other, non-protein secondary components so as to form a single therapeutic agent. For example, the disclosed polypeptides can be combined with additional components such as, for example, superantigens, muramyl dipeptide (MDP), lipopolysaccharide (LPS), or mannose. According to this embodiment, fusion or chimeric therapeutic agents encompassed by the present invention can generally include one or more of the disclosed laminin-5×3α G domain polypeptides linked together with other materials via post-translational modification through covalent bonds such as amide, ester, disulfide or azo bonds, for example.

In general, methods for treatment of disease utilizing the disclosed agents include contacting the cellular pathogen with a composition comprising the polypeptides of the invention. For example, in one embodiment, the methods of the disclosed invention can be utilized in vivo for treatment of a disease such as cancer. According to this embodiment, a composition including the disclosed therapeutic agents and a pharmaceutically compatible carrier can be delivered to a patient via any pharmaceutically acceptable delivery system. For instance, a composition of the present invention including a pharmaceutically compatible carrier and the disclosed polypeptides may be a solid, liquid or aerosol and may be administered by any known pharmaceutically acceptable route of administration. A non-limiting exemplary listing of possible solid compositions can include pills, creams, and implantable dosage units. An implantable dosage unit can, in one embodiment, be administered locally, for example at a tumor site, or can be implanted for systemic release of the composition, for example subcutaneously. A non-limiting exemplary listing of possible liquid compositions can include formulations adapted for injection subcutaneously, intravenously, intraarterially, and formulations for topical and intraocular administration. Possible examples of aerosol formulations include inhaler formulations for direct administration to the lungs.

The proteins and protein fragments of the disclosed invention can be provided as isolated and substantially purified proteins and protein fragments in pharmaceutically acceptable formulations using formulation methods known to those of ordinary skill in the art. These formulations can generally be administered by standard routes. For example, the combinations may be administered by topical, transdermal, intraperitoneal, intracranial, intracerebroventricular, intracerebral, intravaginal, intrauterine, oral, rectal or parenteral (e.g., intravenous, intraspinal, subcutaneous or intramuscular) route. Osmotic minipumps may also be used to provide controlled delivery of high concentrations of the disclosed polypeptides through cannulae to the site of interest, such as directly into a metastatic growth.

Pharmaceutical compositions for parenteral injection according to the present invention include pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyois (e.g., glycerol, propylene glycol, polyethylene glycol and the like), carboxymethylcellulose and suitable mixtures thereof, vegetable oils (e.g., olive oil) and injectable organic esters such as ethyl oleate. In addition, if desired, the composition can contain minor amounts of auxiliary substances such as wetting or emulsifying agents, pH buffering agents and the like which enhance the effectiveness of the active ingredient. Proper fluidity may be maintained, for example, by the use of coating materials such as lecithin, by the maintenance of the required particle size in the case of dispersions and by the use of surfactants. These compositions may also contain adjuvants such as preservatives, wetting agents, emulsifying agents and dispersing agents. Prevention of the action of microorganisms may be ensured by the inclusion of various antibacterial and antifungal agents such as paraben, chlorobutanol, phenol, sorbic acid and the like. It may also be desirable to include isotonic agents such as sugars, sodium chloride and the like.

Prolonged absorption of an injectable pharmaceutical form may be brought about by the inclusion of agents, such as aluminum monostearate and gelatin, which can delay absorption. For example, injectable depot forms can be made by forming microencapsule matrices of the therapeutic agent in biodegradable polymers such as polylactide-polyglycolide, poly(orthoesters) and poly(anhydrides). Depending upon the ratio of therapeutic agent to polymer and the nature of the particular polymer employed, the rate of drug release can be controlled. Depot injectable formulations can also be prepared by entrapping the therapeutic agents in liposomes or microemulsions which are compatible with body tissues. The injectable formulations may be sterilized, for example, by filtration through a bacterial-retaining filter or by incorporating sterilizing agents in the form of sterile solid compositions which can be dissolved or dispersed in sterile water or other sterile injectable media just prior to use.

In one embodiment, the therapeutic compositions of the present invention can include pharmaceutically acceptable salts of the components therein, e.g., those that may be derived from inorganic or organic acids. Pharmaceutically acceptable salts are well known in the art. For example, S. M. Berge, et al. describes pharmaceutically acceptable salts in detail in J. Pharmaceutical Sciences (1977) 66:1 et seq., which is incorporated herein by reference. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. The salts may be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptonoate, hexanoate, fumarate, hydrochloride, hydrobromide, hydroiodide, 2-hydroxymethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl, and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

In one embodiment the treatment method can include use of timed release or sustained release delivery systems as are generally known in the art. Such systems can be desirable, for instance, in situations where surgery is difficult or impossible, e.g., situations involving patients debilitated by age or the disease course itself, or where the risk-benefit analysis dictates control over cure. According to this particular embodiment, a sustained-release matrix can include a matrix made of materials, usually polymers, which are degradable by enzymatic or acid/base hydrolysis or by dissolution. Once inserted into the body, such a matrix can be acted upon by enzymes and body fluids. The sustained-release matrix desirably is chosen from biocompatible materials such as liposomes, polylactides (polylactic acid), polyglycolide (polymer of glycolic acid), polylactide co-glycolide (co-polymers of lactic acid and glycolic acid) polyanhydrides, poly(ortho)esters, polyproteins, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Possible biodegradable polymers and their use are described, for example, in detail in Brem et al. (1991, J. Neurosurg. 74:441-6), which is hereby incorporated by reference in its entirety.

When an effective amount of therapeutic agents of the present invention is administered orally, the therapeutic compositions can be in the form of a tablet, capsule, powder, solution or elixir. When administered in tablet form, the pharmaceutical composition of the invention may additionally contain a solid carrier such as a gelatin or an adjuvant. The tablet, capsule, or powder can, for example, contain from about 5 to 95% therapeutic agents of the present invention. In one embodiment, the composition can contain from about 25 to 90% therapeutic agents of the present invention.

When administered orally in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of therapeutic agents of the present invention, in one embodiment from about 1 to 50% therapeutic agents of the present invention.

When an effective amount of the agents of the present invention are administered by intravenous, cutaneous or subcutaneous injection, the polypeptides of the present invention can generally be in the form of a pyrogen-free, parenterally acceptable aqueous solution. The preparation of such parenterally acceptable polypeptide solutions, having due regard to pH, isotonicity, stability, and the like, is within the skill in the art. A preferred pharmaceutical composition for intravenous, cutaneous, or subcutaneous injection can contain, in addition to the polypeptides of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The dosage of the disclosed polypeptides of the present invention can depend on the disease state or condition being treated and other clinical factors such as weight and condition of the human or animal and the route of administration of the compound. Depending upon the half-life of the disclosed polypeptides in the particular animal or human, the disclosed polypeptides can be administered between several times per day to once a week. It is to be understood that the present invention has application for both human and veterinary use. The methods of the present invention contemplate single as well as multiple administrations, given either simultaneously or over an extended period of time. In addition, the disclosed polypeptides can be administered in conjunction with other forms of therapy, e.g., chemotherapy, radiotherapy, or other immunotherapy.

The present invention may be better understood with respect to the following examples.

EXAMPLE 1

General Methodologies for Construction, Expression, and Isolation of Laminin-5-α3 Peptides Manipulations of DNA were completed according to standard techniques as described by Sambrook, et al., *Molecular Cloning: A Laboratory Manual*, second ed., Cold Spring Harbor Laboratory Press, New York, 1989. Restriction enzymes were purchased from either Promega or New England Biolabs. *Escherichia coli* (*E. coli*) strains DH5αMCR (Jessee and Bloom, 1988), GM2163 (New England Biolabs), and JM109 (Promega) were used throughout and grown in either L. broth (Lennox, 1955) or Terrific Broth (Tartof and Hobbs, 1987). All cultures were grown at 37° C. and liquid cultures were agitated at 250 rpm. Plasmid ligation reactions were performed according to protocols found in Sambrook et al. (1989). Pasmid ligations were transformed into *E. coli* competent cells (from strains DH5αMCR or GM2163) by a heat-shock procedure (Henson, 1984) while transformations into *E. coli* competent cells from strain JM109 were conducted according to the manufacturer's protocol. Plasmid DNA from putative transformants was isolated using a plasmid miniprep system.

Plasmid Construction and Transformation

Two partial cDNA clones from rat laminin-5-α3 cloned into pBluescript SK (Stratagene) were obtained from Northwestern University. Plasmid 5C5 encoded the region of 932-3242 bp of laminin-5 α3 chain region, and, plasmid 3'α3 encoded the 3' half of laminin-5-α3 chain region from 3092-5250 bp. FIG. 4 illustrates the restriction map.

Plasmid pHB1 was constructed from PCR amplification of the 5C5 cDNA (see FIG. 5). For cloning in the vector pGEM-T Easy, the following synthetic oligonucleotide primers were used for PCR amplification: forward (5'-AATTAAC-CCTCACTAAAGGG-3') (SEQ ID NO: 7) and reverse (5'-TAATACGACTCACTATAGGG-3') (SEQ ID NO: 8). The addition of Taq polymerase resulted in poly A-overhangs that were added to the PCR products and purified from 1% agarose gel using the Rapid Plasmid Miniprep System (Marligen Biosciences, Inc). The agarose purified product was ligated into pGEM-T Easy. The ligation reaction was carried out for 4 hours at room temperature. *E. coli* strain GM2163 (New England Biolabs) was transformed (Sambrook, et al 1989) with the ligation product. Proper construction of the final plasmid pHB1 was verified by restriction analysis and DNA sequencing on a Licor 4200L sequencer using T7 and SP6 primers.

Plasmid pHB2 was constructed from PCR amplification of the 3'α3 cDNA. For cloning in the vector pGEM-T Easy, the following synthetic oligonucleotides primers were used for PCR amplification: forward (5'-CCAGACTACTGTGGA-CAGAGG-3') (SEQ ID NO: 9) and reverse (5'-AAGGGT-TCTTCGTGTGTAGGG-3') (SEQ ID NO: 10). Procedures for plasmid construction, transformation and verification were continued as described previously for pHB1.

Plasmid pHB3 was constructed from pHB2 by digesting with XbaI, precipitation, followed by a partial digest with EcoRI. Aliquots were removed in 10 µl volumes every 3 minutes followed by the addition of 1 µl 0.5 M EDTA pH 8.0. Restriction digest products were viewed on 1.5% agarose gel, and the desired 1761 bp fragment was agarose purified as described above. Cloning vector pYES2 was digested by XbaI and EcoRI and ligated with the 1761 bp XbaI/EcoRI partial fragment from pHB2. The ligation reaction was carried out for 24 hours at room temperature and transformed into *E. coli* strain DH5αMCR. Proper construction was verified by restriction enzyme analysis.

Plasmid pHB4 (containing G1-G5 domains of laminin-5-α3) was constructed from pHB1 digest with SacI/EcoRI. The resulting 822 bp fragment from 5C5 was agarose purified. Plasmid pHB3 was digested with SacI, precipitated, followed by an EcoRI partial digest performed as illustrated previously. Restriction digest products were viewed on a 0.7% agarose gel and the desired fragment containing pYES2+ 1761 bp was agarose purified. The 822 bp fragment from pHB1 was ligated with pYES+1761 bp (linearized pHB3) for 24 hours at room temperature and transformed in *E. coli* strain DH5αMCR. Proper construction was verified by restriction enzyme analysis. Internal junctions were sequenced on ABI Prism 3700 DNA Analyzer using the primers: forward (5'-CTACTCAACCAAATGCTCCC-3') (SEQ ID NO: 11) and reverse (5'-GTACTATTCAACCTGACAACCC-3') (SEQ ID NO: 12). Prior to sequencing, dye-terminator removal was completed using Qiagen DyeEX™ 2.0 Spin Kit.

Expression Vector Construction and Transformation in *E. coli*

The expression of recombinant laminin proteins was produced using the EasySelect™ *Pichia* Expression Kit from Invitrogen. Cloning of laminin-5-α3 G domains into the *P. pastoris* expression vector pPICZαB for the construction of pHB6 was performed in a multi-step procedure. pPICZαB was digested with KpnI, followed by a T4 DNA polymerase reaction to blunt 3' overhangs, precipitated, digested with XbaI and the resulting fragment was purified from a 1% agarose gel. The DNA fragment encoding the regions of G1-G5 of laminin-5-α3 chain from pHB4 was digested with SacI, followed by treatment with T4 DNA polymerase, digested with XbaI and also purified from a 1% agarose gel. The ligation reaction was 24 hours at room temperature, followed by transformation in *E. coli* strain JM109 and plated onto low salt LB Zeocin™ plates. Proper construction of the vector pHB6 was verified by restriction analysis and DNA sequencing. The following synthetic oligonucleotides were used: forward AOX1 (5'-GACTGGTTCCAATTGA-CAAGC-3') (SEQ ID NO: 13) and reverse AOX1 (5'-GCAAATGGCATTCTGACATCC-3') (SEQ ID NO: 14).

Construction of pHB7 was performed from *P. pastoris* cloning/expression vector pPICZαB, and the DNA fragment encoding the regions of G3-G5 from pHB6 digestion with EcoRI/XbaI and agarose purified. The ligation reaction, transformation, restriction analysis and DNA sequencing were all conducted as stated above for pHB6.

Production of pHB8 containing laminin-5-α3 plasmid G1-G3 domains in pPICZαB was by removal of the G4 and G5 domain from the plasmid pHB6. This was performed by digestion of pHB6 with XbaI enzyme, treated with T4 DNA polymerase to blunt the 3' overhangs, precipitated, followed by a partial digest with PvuII and agarose purification of a 5304 bp fragment. This linear fragment was religated for 24 hours at room temperature and transformed into *E. coli* strain JM109. Construction of plasmid pHB8 was verified by restriction analysis and DNA sequencing as stated for pHB6.

Construction of plasmid pHB9 included the G3 domain of laminin-5-α3 chain cloned into the expression vector pPICZαB by the following: digestion of the vector with XbaI, treated with T4 DNA polymerase to blunt 3' overhangs, precipitated, digested with EcoRI, and agarose purified. The G3 insert was produced from plasmid pHB7 digested with EcoRI, precipitated, digested with PvuII and agarose purified. Ligation conditions were 24 hours at room temperature and transformed into *E. coli* strain JM109. Verification of correct construction was as stated for pHB6.

Expression in *P. pastoris*

The *P. pastoris* yeast strain SMD1168 was transformed by the *Pichia* EasyComp™ Kit as described from Invitrogen with 5 µg of SacI linearized expression plasmids. Multicopy recombinants were selected on YPDS (yeast extract with peptone, dextrose and sorbitol) plates containing 100 µg/ml Zeocin™. Loss of the AOX1 gene results in a strain that is referred to as Mut$^s$, which is designated to describe the phenotype of such mutants that lack the ability to metabolize methanol. Cells described as the Mut$^+$ phenotype are capable of utilizing methanol as the sole carbon source. These phenotypes are commonly used to evaluate the *P. pastoris* transformants for correct integration into the genome. Transformants were screened for their ability to grow on histidine-deficient minimal dextrose agar plates which confirmed the Mut$^+$ phenotype.

Analysis of Recombinant Laminin

For verification of gene integration into the *P. pastoris* genome, genomic DNA was isolated and analyzed by PCR. Single colonies from the YPDS-Zeocin™ plates were used to inoculate 5 ml overnight cultures in YPD (1% yeast extract, 2% peptone, 2% dextrose) medium. The isolation of genomic DNA was performed by the Rather Rapid Genomic Prep protocol (Hoffman and Winston, Rather Rapid Genomic Prep, *Gene*, Vol. 87:262-272, 1987). Direct PCR screening of *P. pastoris* clones was carried out using the synthetic oligonucleotides encoding the 5' AOX1 (942 bp fragment containing the AOX1 promoter that allows methanol-inducible, high level expression in *P. pastoris*) and 3' AOX1 regions using the same primers described previously in the expression vector construction.

High-cell Density Expression of Recombinant *P. pastoris* Strains

Expression of the recombinant laminin protein was carried out in a BioFlo 110 Modular Benchtop Fermentor (New Brunswick Scientific) with a total volume of 2.0 L. The dissolved oxygen was kept at 30% of saturation until feed phase, this was maintained at >40%. The dissolved oxygen was controlled by the agitation rate. Total inlet gas flow was kept >2 wm (v=volume of air in ml, v=per unit of medium in L, m=per unit of time in hours). The pH was maintained at 5.0 by the addition of NH$_4$OH which also served as a minor nitrogen source. The temperature was constant during the fermentation at 30° C.

The innoculum was prepared from 1 ml pre-cultures stored at −80° C. in glycerol with an OD$_{600}$ of 35.0. This was resuspended in 5 ml of 1% BMGY medium and incubated at 30° C. for 4 hours at 250 rpm. Media containing 1% BMGY includes 1% glycerol, 100 mM potassium phosphate, pH 6.0, 1.34% YNB (yeast nitrogen base) and 4×10$^{-5}$% biotin. The culture was used to inoculate 100 ml of overnight medium for an initial OD$_{600}$ of 0.5. Overnight medium was 1% BMGY with the addition of 100 µg/ml of Zeocin™. Incubation continued using the same conditions as before for 11 hour growth. The batch phase was the initial phase in the BioFlo fermentor using 900 ml of batch medium with the addition of the 100 ml innoculum. Batch medium (1 L) consisted of 12 g glycerol, 100 ml 10×YNB (13.4% yeast nitrogen base with ammonium sulfate without amino acids), 100 ml 1 M potassium phosphate, pH 6.0, 2 ml 500× biotin, 1 ml 1000× trace metals, and 786 ml milliQ water. The batch phase lasted 20 hours. During the glycerol fed-batch phase over the next 18 hours, a continuous feed of 444 g glycerol, 100 ml 10×YNB, 1 ml 1000× trace metals, 2 ml 500× biotin and antifoam were added. The total volume of medium added was 474 ml. The methanol fed-batch phase (induction) continued for 20 hours with a medium volume of 203 ml added. This induction medium was comprised of 200 ml 100% MeOH, 1 ml 1000× trace metals and 2 ml 500× biotin. Trace metal components for all media above contained the following per liter: 2.0 g $CuSO_4$, 0.1 g KI, 3.0 g $MnSO_4.H_2O$, 0.2 g $Na_2MoO_4.2H_2O$, 0.02 g boric acid, 0.5 g $CoCl_2$, 7.0 g $ZnCl$, 10.0 g $FeSO_4.H2O$.

Purification of Recombinant Laminin

The supernatant containing recombinant laminin-5 G domains was collected by centrifugation at 5000×g for 10 min. Purification chromatography was performed using 10 g of Sephadex™ G-75 superfine (20-50 micron particle diameter) suspended in 500 ml of 0.1 M ammonium acetate pH 6.95. The suspension was allowed to equilibrate overnight. The swelled gel was degassed for 4 hours and packed into a 1 cm×40 cm Pharmacia column equipped with plastic frit, 10μ filter disk and flow valve. The gel was allowed to settle at full flow rate under gravity. The column was packed to a height of 28 cm with the G-75. Void volume was determined using 3 ml of 2 mg/ml blue dextran (MW>2×10$^6$ Daltons) in PBS containing 1% glycerol. The sample was applied by underlayering and the column was eluded with 0.1 M ammonium acetate until the blue dextran began to emerge (25 ml) and continued until all of the blue dextran had washed from the column (31 ml total). The sample containing 2.5 mg/ml of protein in a 2 ml supernatant plus 1 ml of ammonium acetate was applied to the column as given above. The void volume was obtained as above followed by an additional total column volume of 85 ml that was collected containing the desired recombinant protein of laminin-5. This sample was freeze dried, resuspended in 1 ml total volume of dd$H_2O$ and used for functional assays.

EXAMPLE 2

Adhesion characteristics of MDA-MB-435 breast cancer cells to recombinant (r) rat laminin-5 α3 chain G3 domain protein (SEQ ID NO:6) were examined.

Initially, untreated 96-well plates were coated overnight at 4° C. with purified recombinant rat laminin-5 α3 chain G3 domain protein (SEQ ID NO:6). Various concentrations of the G3 domain protein were added to triplicate wells. Specifically, concentrations examined included 0.1, 0.5, 1.0, 2.5, 5.0, 7.5 and 10 μg/ml diluted in sterile PBS. Following overnight coating, wells were washed twice with PBS and blocked for 1 hour at room temperature with 1% BSA/PSA.

MDA-MB-435 breast cancer cells were collected by brief trypsinization, washed twice with culture medium, and plated in the prepared wells including control wells that had not been coated with the G3 domain protein, at 5×10$^5$ cells/well. Plates were incubated for 1 hour in a 37° C. humidified incubator (5% $CO_2$). After incubation, wells were washed with medium twice to remove unbound cells, followed by fixing attached cells with 3.7% paraformaldehyde/PBS for 10 minutes, and then staining attached cells with 0.5% crystal violet solution. At the end of 10 minutes staining, wells were washed twice with dd$H_2O$ to remove excess dye followed by addition of 1% SDS to solubilize cells. The amount of crystal violet incorporated into attached cells was determined using a Molecular Devices plate reader set to absorb at 550 nm.

Figure 6:
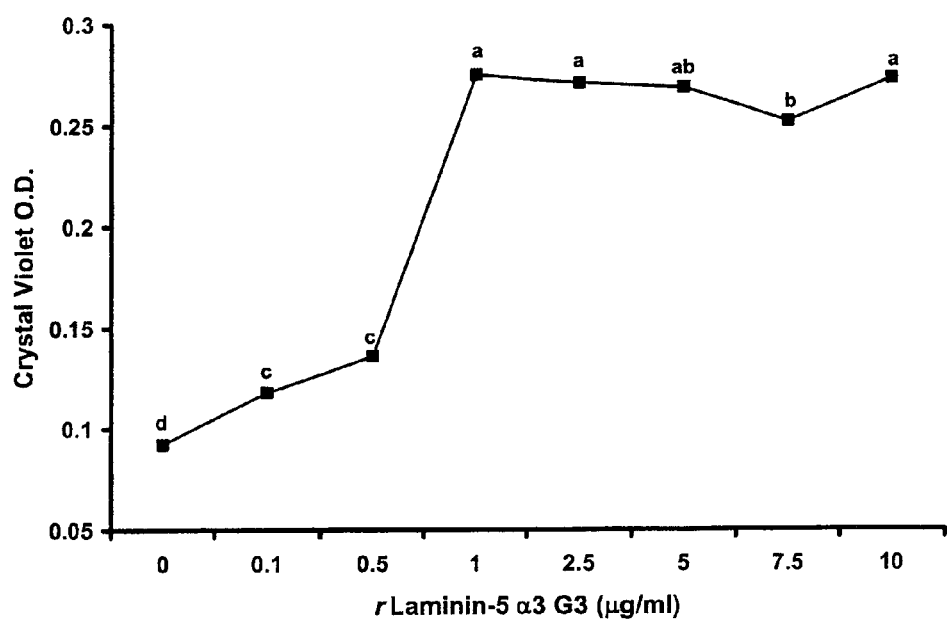
FIG. 6 graphically illustrates the level of crystal violet incorporation by MDA-MB-435 breast cancer cells bound to recombinant (r) laminin-5 α3 chain G3 domain protein (SEQ ID NO:6) following coating of the protein to plate wells at various concentrations.

FIG. 6 graphically illustrates the results. Mean O.D. readings labeled on the graph with different letters are significantly different at P≦0.0001.

EXAMPLE 3

Well plates were coated overnight at 4° C. with purified recombinant rat laminin-5 α3 chain G3 domain protein (SEQ ID NO:6) as described above with all coated wells coated at 5.0 μg/ml diluted in sterile PBS. Following overnight coating, wells were washed twice with PBS and blocked for 1 hour at room temperature with 1% BSA/PSA.

MDA-MB-435 breast cancer cells were collected by brief trypsinization and washed twice with culture medium. The MDA-MB-435 cells were split into three portions, one portion was plated as described above in Example 2 at 5×10$^5$ cells/well in wells previously coated with 5.0 μg/ml G3 domain protein (labeled G3 on FIG. 7) and also plated into otherwise untreated well plates (labeled Control on FIG. 7). The other two portions were incubated prior to plating with either anti-α6 integrin monoclonal antibody or mouse IgG2a isotype control at a 1:5 dilution for 15 minutes. Following incubation, these portions were also plated in wells previously coated with 5 μg/ml of the G3 protein according to the process described above in Example 2 at 5×10$^5$ cells/well (labeled G3+Anti-alph6 and G3+IgG2a, respectively, on FIG. 7) and also were plated in untreated well plates, i.e., wells not previously coated with the G3 protein (labeled Anti-alpha6 and IgG2a on FIG. 7, respectively).

All plates were incubated for 1 hour in a 37° C. humidified incubator (5% $CO_2$). After incubation, wells were washed with medium twice to remove unbound cells, followed by fixing attached cells with 3.7% paraformaldehyde/PBS for 10 minutes, and then staining attached cells with 0.5% crystal violet solution. At the end of 10 minutes staining, wells were washed twice with dd$H_2O$ to remove excess dye followed by addition of 1% SDS to solubilize cells. The amount of crystal violet incorporated into attached cells was determined using a Molecular Devices plate reader set to absorb at 550 nm.

Figure 7:
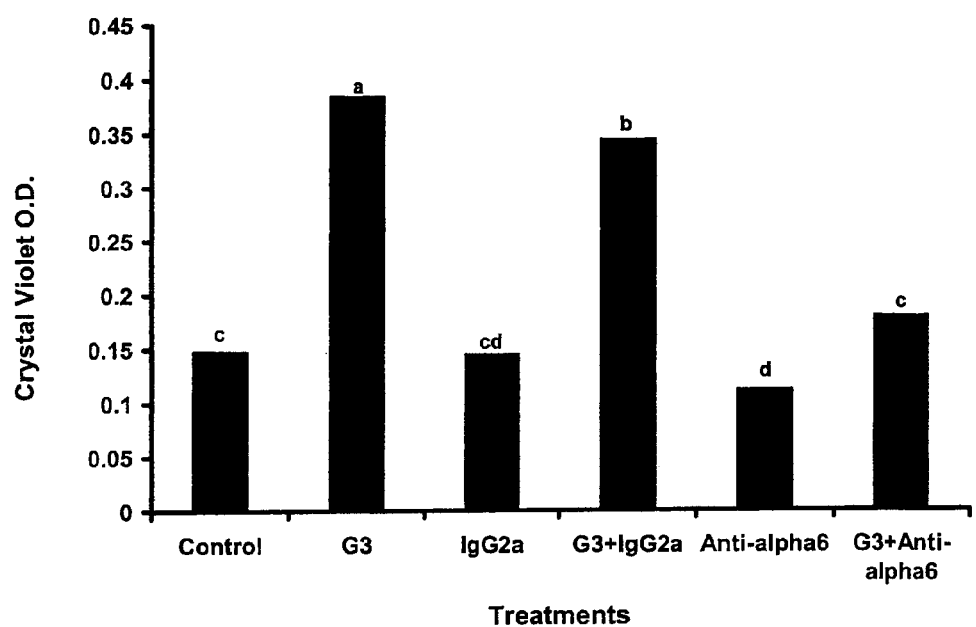
FIG. 7 graphically illustrates the level of crystal violet incorporation by MDA-MB-435 breast cancer cells bound to recombinant (r) rat laminin-5 α3 chain G3 domain protein (SEQ ID NO:6) following coating of the protein to plate wells at various concentrations. Portions of the breast cancer cells were incubated with either anti-α6 integrin monoclonal antibody or mouse IgG2a isotype prior to plating.

FIG. 7 graphically illustrates the results. Mean O.D. readings labeled on the graph with different letters are significantly different at P≦0.0001.

EXAMPLE 4

Purified recombinant rat laminin-5 α3 chain G3 domain protein (SEQ ID NO:6) was added in increasing concentrations to wells of 96-well plates as described above. Specifically, the concentrations of G3 domain protein added to wells were 1.0, 2.5, 5.0, 7.5, 10 and 15 μg/ml diluted in culture medium.

MDA-MB-435 cells were collected by brief trypsinization, washed twice with culture medium, and plated at 5×10$^5$ cells/well in the prepared wells as well as in control wells not coated with the G3 domain protein. Plates were incubated for 24 hours at 37° C. in a humidified incubator (5% $CO_2$). Twenty μl of MTT (3-[4,5-dimethlythiozol-2-yl]-2,5-diphenyltetrazolium bromide) reagent (5 mg/ml) was added to all wells during the final 4 hours of incubation. One hundred μl of culture supernatant was removed from each well followed by the addition of 100 μl dimethylsulfoxide (DMSO) to solubilize the cells. Plates were shaken for 15 minutes and absorbance was recorded at dual wavelengths of 570/650 nm using a Molecular Devices plate reader to examine the proliferation of the cancer cells in the wells.

Figure 8:
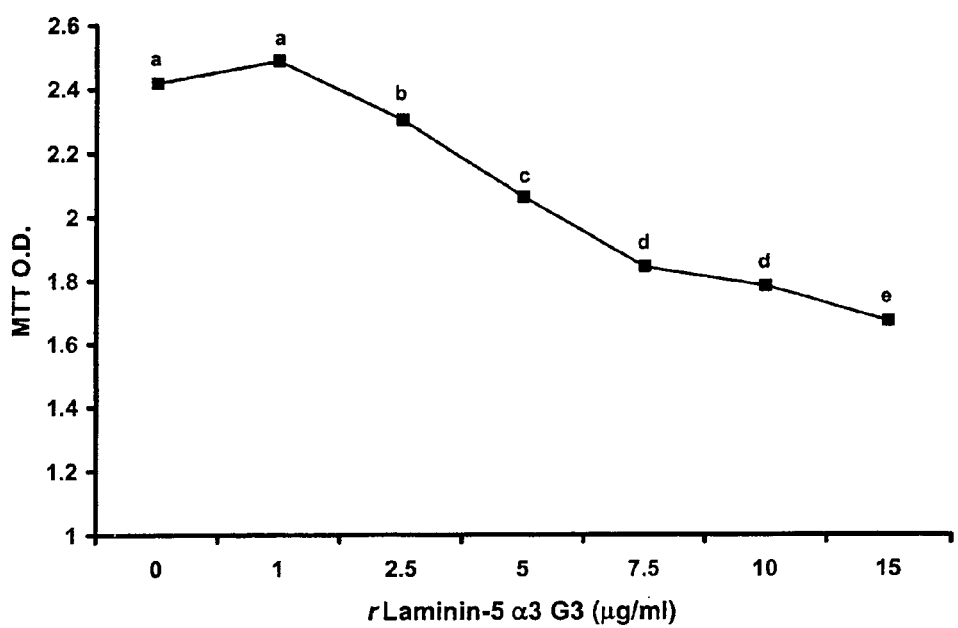
FIG. 8 graphically illustrates cell proliferation of MDA-MB-435 breast cancer cells following binding of the cancer cells to recombinant (r) rat laminin-5 α3 chain G3 domain protein (SEQ ID NO:6).

FIG. 8 illustrates the results. Mean O.D. readings labeled on the graph with different letters are significantly different at P≦0.0001. As can be seen, cancer cell proliferation declined with increasing dosage level of the G3 domain protein composition.

EXAMPLE 5

Well plates were coated overnight at 4° C. with purified recombinant rat laminin-5 α3 chain G3 domain protein (SEQ ID NO:6) as described above with all coated wells coated at 10.0 μg/ml diluted in sterile PBS. Following overnight coating, wells were washed twice with PBS and blocked for 1 hour at room temperature with 1% BSA/PSA.

MDA-MB-435 breast cancer cells were collected by brief trypsinization and washed twice with culture medium. The MDA-MB-435 cells were split into three portions, one portion was plated as described above in Example 4 at $5 \times 10^5$ cells/well in wells previously coated with 10.0 μg/ml G3 domain protein (labeled G3 on FIG. 9) and also plated into otherwise untreated well plates (labeled Control on FIG. 9). The other two portions were incubated prior to plating with either anti-α6 integrin monoclonal antibody or mouse IgG2a isotype control at a 1:10 dilution for 15 minutes. Following incubation, these portions were plated in wells previously coated with 10 μg/ml of the G3 protein according to the process described above in Example 2 at $5 \times 10^5$ cells/well (labeled G3+Anti-alph6 and G3+IgG2a, respectively, on FIG. 9) and also were plated in untreated well plates, i.e., wells not previously coated with the G3 protein (labeled Anti-alpha6 and IgG2a on FIG. 9, respectively).

Plates were incubated for 24 hours at 37° C. in a humidified incubator (5% $CO_2$). Twenty μl of MTT (3-[4,5-dimethylthiozol-2-yl]-2,5-diphenyltetrazolium bromide) reagent (5 mg/ml) was added to all wells during the final 4 hours of incubation. One hundred μl of culture supernatant was removed from each well followed by the addition of 100 μl dimethylsulfoxide (DMSO) to solubilize the cells. Plates were shaken for 15 minutes and absorbance was recorded at dual wavelengths of 570/650 nm using a Molecular Devices plate reader to examine the proliferation of the cancer cells in the wells.

Figure 9:
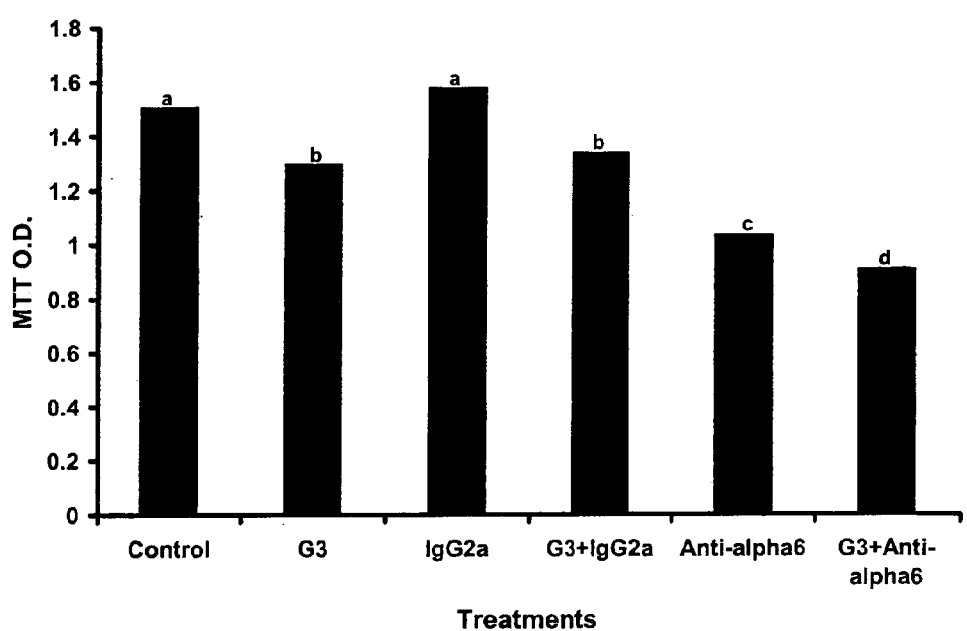
FIG. 9 graphically illustrates cell proliferation of MDA-MB-435 breast cancer cells following binding of the cancer cells to recombinant (r) rat laminin-5 α3 chain G3 domain protein (SEQ ID NO:6). Portions of the breast cancer cells were incubated with either anti-α6 integrin monoclonal antibody or mouse IgG2a isotype prior to plating.

FIG. 9 illustrates proliferation results. Mean O.D. readings labeled on the graph with different letters are significantly different at P<0.0001. As can be seen, proliferation declined with the G3 domain protein and with the anti-α6 integrin monoclonal antibody, with the combination of the two exhibiting the best results.

It will be appreciated that the foregoing examples, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention which is defined in the following claims and all equivalents thereto. Further, it is identified that many embodiments may be conceived that do not achieve all of the advantages of some embodiments, yet the absence of a particular advantage shall not be construed to necessarily mean that such an embodiment is outside the scope of the present invention.

What is claimed is:

1. A method comprising:
   delivering a purified agent to a breast cancer cell, the purified agent including a polypeptide component consisting of the G3 subdomain of laminin-5 α3 chain, the G3 subdomain binding at least one of α6β1 and α6β4 integrin receptors;
   binding the agent to the breast cancer cell, wherein the breast cancer cell includes at least one of α6β1 and α6β4 integrin receptors on a surface of the breast cancer cell; and
   wherein upon binding the purified agent to the breast cancer cell, the proliferation of the breast cancer cell declines.

2. The method according to claim 1, wherein the G3 subdomain of the laminin-5 α3 chain is SEQ ID NO:6.

3. The method according to claim 1, wherein the purified agent consists of the G3 subdomain of the laminin-5 α3 chain.

4. The method according to claim 3, wherein the agent is a recombinant polypeptide.

5. The method according to claim 1, wherein the agent further comprises a second component bound to the first component.

6. The method according to claim 5, wherein the second component is a polypeptide.

7. The method according to claim 6, wherein the agent is a recombinant polypeptide.

8. The method according to claim 1, further comprising providing the purified agent as a constituent of a composition.

9. The method according to claim 8, the composition further comprising a biologically compatible constituent.

10. A method comprising:
    delivering a purified agent to a breast cancer cell, the purified agent including a polypeptide component consisting of the G1-G3 subdomain of laminin-5 α3 chain, the polypeptide component binding at least one of α6β1 and α6β4 integrin receptors;
    binding the agent to the breast cancer cell, wherein the breast cancer cell includes at least one of α6β1 and α6β4 integrin receptors on a surface of the breast cancer cell; and
    wherein upon binding the purified agent to the breast cancer cell, the proliferation of the breast cancer cell declines.

11. The method according to claim 10, wherein the G1-G3 subdomain of the laminin-5 α3 chain is SEQ ID NO:4.

12. The method according to claim 10, wherein the agent consists of the G1-G3 subdomain of the laminin-5 α3 chain.

13. The method according to claim 12, wherein the agent is a recombinant polypeptide.

14. The method according to claim 10, wherein the agent further comprises a second component bound to the first component.

15. The method according to claim 14, wherein the second component is a polypeptide.

16. The method according to claim 15, wherein the agent is a recombinant polypeptide.

17. The method according to claim 10, further comprising providing the purified agent as a constituent of a composition.

18. The method according to claim 17, the composition further comprising a biologically compatible constituent.

19. A method comprising:
    delivering a purified agent to a breast cancer cell, the purified agent including a polypeptide component consisting of the complete globular domain of laminin-5α3 chain, the polypeptide component binding at least one of α6β1 and α6β4 integrin receptors;
    binding the agent to the breast cancer cell, wherein the breast cancer cell includes at least one of the α6β1 and α6β4 integrin receptors on a surface of the breast cancer cell; and
    wherein upon binding the purified agent to the breast cancer cell, the proliferation of the breast cancer cell declines.

20. The method according to claim 19, wherein the complete globular domain is SEQ ID NO:2.

21. The method according to claim 19, wherein the agent consists of the complete globular domain of laminin-5α3 chain.

22. The method according to claim 21, wherein the agent is a recombinant polypeptide.

23. The method according to claim 19, wherein the agent further comprises a second component bound to the first component.

24. The method according to claim 23, wherein the second component is a polypeptide.

25. The method according to claim 24, wherein the agent is a recombinant polypeptide.

26. The method according to claim 19, further comprising providing the purified agent as a constituent of a composition.

27. The method according to claim 26, the composition further comprising a biologically compatible constituent.

28. The method according to claim 10 in which the purified agent comprises SEQ ID NO. 6.

29. The method according to claim 19, in which the purified agent comprises SEQ ID NO. 6.

* * * * *

SEQUENCE LISTING

<160> NUMBER OF SEQ ID NOS: 14

<210> SEQ ID NO 1
<211> LENGTH: 2647
<212> TYPE: DNA
<213> ORGANISM: Rattus norvegicus
<220> FEATURE:
<221> NAME/KEY: CDS
<222> LOCATION: (48)..(2645)

<400> SEQUENCE: 1

```
gagctcattc gcaggccaga gatgctgcga acaaggttgc aattccc atg agg ttc      56
                                                    Met Arg Phe
                                                     1 aat ggt aaa tct ggt gtt gaa gtc cgt ctg cca aat gac cta gaa gac     104
Asn Gly Lys Ser Gly Val Glu Val Arg Leu Pro Asn Asp Leu Glu Asp
      5                  10                  15 ttg aag gga tac acg tct ctg tct ttg ttc ctc caa aga cca gac tta     152
Leu Lys Gly Tyr Thr Ser Leu Ser Leu Phe Leu Gln Arg Pro Asp Leu
 20                  25                  30                  35 aga gag aat gga ggc act gag gac atg ttt gta atg tac ctt gga aac     200
Arg Glu Asn Gly Gly Thr Glu Asp Met Phe Val Met Tyr Leu Gly Asn
                 40                  45                  50 aag gat gcc tcc aag gac tac atc ggc atg gcg gtt gta gat ggc cag     248
Lys Asp Ala Ser Lys Asp Tyr Ile Gly Met Ala Val Val Asp Gly Gln
             55                  60                  65 ctg acg tgt gtc tac aac ctg ggg gac cga gaa gct gaa gtt cag atc     296
Leu Thr Cys Val Tyr Asn Leu Gly Asp Arg Glu Ala Glu Val Gln Ile
         70                  75                  80
```

| | | | | | | | | | | | | | | | | |
|---|---|---|---|---|---|---|---|---|---|---|---|---|---|---|---|---|
| gat | cag | gtc | ctg | acg | gag | agt | gag | tct | cag | gag | gca | gtt | atg | gac | cgg | 344 |
| Asp | Gln | Val | Leu | Thr | Glu | Ser | Glu | Ser | Gln | Glu | Ala | Val | Met | Asp | Arg | |
| | 85 | | | | 90 | | | | | 95 | | | | | | |
| gtg | aag | ttc | cag | aga | ata | tat | caa | ttt | gcc | aag | ctt | aat | tac | acc | aaa | 392 |
| Val | Lys | Phe | Gln | Arg | Ile | Tyr | Gln | Phe | Ala | Lys | Leu | Asn | Tyr | Thr | Lys | |
| 100 | | | | | 105 | | | | | 110 | | | | | 115 | |
| gaa | gcc | acg | tcc | aat | aaa | ccc | aaa | gct | ccc | gcg | gtc | tac | gac | ctg | gag | 440 |
| Glu | Ala | Thr | Ser | Asn | Lys | Pro | Lys | Ala | Pro | Ala | Val | Tyr | Asp | Leu | Glu | |
| | | | | 120 | | | | | 125 | | | | | 130 | | |
| ggt | ggc | agt | agc | aac | acg | ctc | ctt | aat | ttg | gat | ccc | gag | gac | gct | gtg | 488 |
| Gly | Gly | Ser | Ser | Asn | Thr | Leu | Leu | Asn | Leu | Asp | Pro | Glu | Asp | Ala | Val | |
| | | | 135 | | | | | 140 | | | | | 145 | | | |
| ttt | tat | gtc | gga | ggt | tac | cca | ccg | gat | ttt | gaa | ctt | cct | agc | aga | ctg | 536 |
| Phe | Tyr | Val | Gly | Gly | Tyr | Pro | Pro | Asp | Phe | Glu | Leu | Pro | Ser | Arg | Leu | |
| | | 150 | | | | | 155 | | | | | 160 | | | | |
| cgg | ttc | cct | cca | tac | aaa | ggc | tgt | atc | gaa | cta | gat | gac | ctc | aat | gaa | 584 |
| Arg | Phe | Pro | Pro | Tyr | Lys | Gly | Cys | Ile | Glu | Leu | Asp | Asp | Leu | Asn | Glu | |
| | 165 | | | | | 170 | | | | | 175 | | | | | |
| aac | gtt | cta | agc | ttg | tac | aat | ttc | aag | aca | act | ttc | aat | ctc | aac | acc | 632 |
| Asn | Val | Leu | Ser | Leu | Tyr | Asn | Phe | Lys | Thr | Thr | Phe | Asn | Leu | Asn | Thr | |
| 180 | | | | | 185 | | | | | 190 | | | | | 195 | |
| acg | gag | gtg | gag | cct | tgt | agg | agg | aga | aag | gaa | gag | tca | gac | aaa | aat | 680 |
| Thr | Glu | Val | Glu | Pro | Cys | Arg | Arg | Arg | Lys | Glu | Glu | Ser | Asp | Lys | Asn | |
| | | | | 200 | | | | | 205 | | | | | 210 | | |
| tac | ttt | gaa | ggt | aca | ggc | tat | gct | cgc | atc | cct | act | caa | cca | aat | gct | 728 |
| Tyr | Phe | Glu | Gly | Thr | Gly | Tyr | Ala | Arg | Ile | Pro | Thr | Gln | Pro | Asn | Ala | |
| | | | 215 | | | | | 220 | | | | | 225 | | | |
| ccc | ttc | cca | aac | ttc | ata | cag | acc | atc | cag | act | act | gtg | gac | aga | ggt | 776 |
| Pro | Phe | Pro | Asn | Phe | Ile | Gln | Thr | Ile | Gln | Thr | Thr | Val | Asp | Arg | Gly | |
| | | 230 | | | | | 235 | | | | | 240 | | | | |
| tta | ctg | ttc | ttc | gca | gaa | aac | cag | gat | aac | ttc | ata | tct | ctg | aac | ata | 824 |
| Leu | Leu | Phe | Phe | Ala | Glu | Asn | Gln | Asp | Asn | Phe | Ile | Ser | Leu | Asn | Ile | |
| | 245 | | | | | 250 | | | | | 255 | | | | | |
| gaa | gat | ggc | aat | ctc | atg | gtg | aga | tac | aaa | cta | aat | tca | gag | cca | ccc | 872 |
| Glu | Asp | Gly | Asn | Leu | Met | Val | Arg | Tyr | Lys | Leu | Asn | Ser | Glu | Pro | Pro | |
| 260 | | | | | 265 | | | | | 270 | | | | | 275 | |
| aaa | gag | aag | gga | att | cga | gac | acc | atc | aac | gat | ggg | aaa | gat | cat | tcg | 920 |
| Lys | Glu | Lys | Gly | Ile | Arg | Asp | Thr | Ile | Asn | Asp | Gly | Lys | Asp | His | Ser | |
| | | | | 280 | | | | | 285 | | | | | 290 | | |
| atc | tta | atc | aca | att | gga | aaa | cta | caa | aaa | cgc | atg | tgg | ata | aat | gtg | 968 |
| Ile | Leu | Ile | Thr | Ile | Gly | Lys | Leu | Gln | Lys | Arg | Met | Trp | Ile | Asn | Val | |
| | | | 295 | | | | | 300 | | | | | 305 | | | |
| aac | gaa | cgc | agt | gta | cga | atc | gaa | ggg | gaa | ata | ttt | gat | ttc | agc | aca | 1016 |
| Asn | Glu | Arg | Ser | Val | Arg | Ile | Glu | Gly | Glu | Ile | Phe | Asp | Phe | Ser | Thr | |
| | | 310 | | | | | 315 | | | | | 320 | | | | |
| tat | tat | ttg | ggc | gga | att | cca | att | gca | atc | aga | gaa | agg | ttt | aac | atc | 1064 |
| Tyr | Tyr | Leu | Gly | Gly | Ile | Pro | Ile | Ala | Ile | Arg | Glu | Arg | Phe | Asn | Ile | |
| | 325 | | | | | 330 | | | | | 335 | | | | | |
| tca | acg | cct | gct | ttc | caa | ggc | tgc | atg | aag | aat | ctg | aag | aaa | acc | agt | 1112 |
| Ser | Thr | Pro | Ala | Phe | Gln | Gly | Cys | Met | Lys | Asn | Leu | Lys | Lys | Thr | Ser | |
| 340 | | | | | 345 | | | | | 350 | | | | | 355 | |
| ggg | gtt | gtc | agg | ttg | aat | gat | act | gtg | ggt | gta | acc | aag | aag | tgc | tca | 1160 |
| Gly | Val | Val | Arg | Leu | Asn | Asp | Thr | Val | Gly | Val | Thr | Lys | Lys | Cys | Ser | |
| | | | | 360 | | | | | 365 | | | | | 370 | | |
| gaa | gac | tgg | aag | ctt | gtg | cga | acc | gcc | tcg | ttc | tcc | aga | gga | ggg | cag | 1208 |
| Glu | Asp | Trp | Lys | Leu | Val | Arg | Thr | Ala | Ser | Phe | Ser | Arg | Gly | Gly | Gln | |
| | | | 375 | | | | | 380 | | | | | 385 | | | |
| atg | agc | ttt | aca | aac | ttg | gac | gtg | ccc | tcg | act | gac | cgc | ttc | cag | ctc | 1256 |
| Met | Ser | Phe | Thr | Asn | Leu | Asp | Val | Pro | Ser | Thr | Asp | Arg | Phe | Gln | Leu | |
| | | 390 | | | | | 395 | | | | | 400 | | | | |

```
tcc ttt ggg ttt cag acc ttt caa ccc agt ggc aca ctg ctc aat cat    1304
Ser Phe Gly Phe Gln Thr Phe Gln Pro Ser Gly Thr Leu Leu Asn His
    405                 410                 415 cag acg cgg aca agc agc ctg ctg gtc acc ctg gaa gat ggg cac att    1352
Gln Thr Arg Thr Ser Ser Leu Leu Val Thr Leu Glu Asp Gly His Ile
420                 425                 430                 435 gag ttg agc act agg gac agc aac atc cca att ttc aag tct cca ggg    1400
Glu Leu Ser Thr Arg Asp Ser Asn Ile Pro Ile Phe Lys Ser Pro Gly
                440                 445                 450 acc tac atg gac ggt tta ctg cat cat gta tct gta ata agt gac acc    1448
Thr Tyr Met Asp Gly Leu Leu His His Val Ser Val Ile Ser Asp Thr
            455                 460                 465 tca ggt ctc cgc ctt ctc atc gat gac cag gtc ctg aga agg aac cag    1496
Ser Gly Leu Arg Leu Leu Ile Asp Asp Gln Val Leu Arg Arg Asn Gln
        470                 475                 480 agg ctt cct agc ttc tct aac gcc cag cag tcg ctc cgc ctt gga gga    1544
Arg Leu Pro Ser Phe Ser Asn Ala Gln Gln Ser Leu Arg Leu Gly Gly
    485                 490                 495 ggt cat ttc gag ggt tgt atc agc aat gtt tta gtc caa agg ttt tca    1592
Gly His Phe Glu Gly Cys Ile Ser Asn Val Leu Val Gln Arg Phe Ser
500                 505                 510                 515 cag agt cca gaa gtc ctg gat ctg gcc agt aaa tct acc aag aag gat    1640
Gln Ser Pro Glu Val Leu Asp Leu Ala Ser Lys Ser Thr Lys Lys Asp
                520                 525                 530 gca tcc cta gga ggc tgc agt tta aac aag cca cct ttt ctt atg ttg    1688
Ala Ser Leu Gly Gly Cys Ser Leu Asn Lys Pro Pro Phe Leu Met Leu
            535                 540                 545 ttt aaa agt ccc aag aga ttt aac aag ggc cgg att ttc aat gtt aat    1736
Phe Lys Ser Pro Lys Arg Phe Asn Lys Gly Arg Ile Phe Asn Val Asn
        550                 555                 560 cag ctg atg caa gat gca cct cag gcc aca agg agc aca gag gct tgg    1784
Gln Leu Met Gln Asp Ala Pro Gln Ala Thr Arg Ser Thr Glu Ala Trp
    565                 570                 575 caa gat ggg agg tcc tgc cta cca cct ctg aac acc aag gcc tct cac    1832
Gln Asp Gly Arg Ser Cys Leu Pro Pro Leu Asn Thr Lys Ala Ser His
580                 585                 590                 595 aga gcc ctg cag ttt gga gac agc ccc acc agc cac ttg cta ctc aag    1880
Arg Ala Leu Gln Phe Gly Asp Ser Pro Thr Ser His Leu Leu Leu Lys
                600                 605                 610 ctt ccc cag gaa ctg ctg aaa cct agg tca cag ttt tct tta gac ata    1928
Leu Pro Gln Glu Leu Leu Lys Pro Arg Ser Gln Phe Ser Leu Asp Ile
            615                 620                 625 cag aca act tcc ccc aaa gga ctg gtg ttt tac gca ggc acc aag gac    1976
Gln Thr Thr Ser Pro Lys Gly Leu Val Phe Tyr Ala Gly Thr Lys Asp
        630                 635                 640 tcc ttc ctg gct ctt tat gtc gca gat ggc cgt gtt gtc ttt gct ttg    2024
Ser Phe Leu Ala Leu Tyr Val Ala Asp Gly Arg Val Val Phe Ala Leu
    645                 650                 655 ggg gca gga ggg aag aaa ctg aga ctc agg agc aag gag aga tac cat    2072
Gly Ala Gly Gly Lys Lys Leu Arg Leu Arg Ser Lys Glu Arg Tyr His
660                 665                 670                 675 gac ggg aag tgg cac acg gtg gtg ttc gga cta aat gga gga aag gca    2120
Asp Gly Lys Trp His Thr Val Val Phe Gly Leu Asn Gly Gly Lys Ala
                680                 685                 690 cgc ctg gtt gtg gat ggg cta agg gcc cag gaa ggc agt ttg cct gga    2168
Arg Leu Val Val Asp Gly Leu Arg Ala Gln Glu Gly Ser Leu Pro Gly
            695                 700                 705 aat tct acc atc agc ccc aga gaa cag gtt tac cta ggg ttg ccg cta    2216
Asn Ser Thr Ile Ser Pro Arg Glu Gln Val Tyr Leu Gly Leu Pro Leu
        710                 715                 720
```

| | | | | | | | | | | | | | | |
|---|---|---|---|---|---|---|---|---|---|---|---|---|---|---|
| tca | aga | aag | cca | aag | agc | cta | ccc | cag | cac | agt | ttt | gtg | ggg | tgc | ctg | 2264 |
| Ser | Arg | Lys | Pro | Lys | Ser | Leu | Pro | Gln | His | Ser | Phe | Val | Gly | Cys | Leu | |
| 725 | | | | 730 | | | | | 735 | | | | | 740 | | |

```
tca aga aag cca aag agc cta ccc cag cac agt ttt gtg ggg tgc ctg      2264
Ser Arg Lys Pro Lys Ser Leu Pro Gln His Ser Phe Val Gly Cys Leu
725             730                 735 aga gat ttc cag ttg aac tcg aaa ccc ctg gat tct cct tct gcg agg      2312
Arg Asp Phe Gln Leu Asn Ser Lys Pro Leu Asp Ser Pro Ser Ala Arg
740             745                 750                 755 ttt ggg gta tct ccc tgc ttg ggt ggc tct tta gag aaa ggc att tat      2360
Phe Gly Val Ser Pro Cys Leu Gly Gly Ser Leu Glu Lys Gly Ile Tyr
                760                 765                 770 ttc tcc caa gga gga ggc cat gtg atc cta gcc aat tct gtg tcc ttg      2408
Phe Ser Gln Gly Gly Gly His Val Ile Leu Ala Asn Ser Val Ser Leu
            775                 780                 785 ggg cca gag ctt aag ctc act ttc agc att cgc cca cgg agt ctc act      2456
Gly Pro Glu Leu Lys Leu Thr Phe Ser Ile Arg Pro Arg Ser Leu Thr
        790                 795                 800 ggg gtc tta ata cac gtc gga agt caa tct gga cag cgc tta agt gtg      2504
Gly Val Leu Ile His Val Gly Ser Gln Ser Gly Gln Arg Leu Ser Val
    805                 810                 815 tac atg gag gca gga aag gtc aca acc tct gtg agc agt gat gca gga      2552
Tyr Met Glu Ala Gly Lys Val Thr Thr Ser Val Ser Ser Asp Ala Gly
820                 825                 830                 835 gga agt gtg aca tca att aca ccg aag cag tct ctg tgt gat gga cag      2600
Gly Ser Val Thr Ser Ile Thr Pro Lys Gln Ser Leu Cys Asp Gly Gln
                840                 845                 850 tgg cac tcg gtg gca gtc tcc att aaa cag cgc atc ctg cat cta ga       2647
Trp His Ser Val Ala Val Ser Ile Lys Gln Arg Ile Leu His Leu
                855                 860                 865
```

<210> SEQ ID NO 2
<211> LENGTH: 866
<212> TYPE: PRT
<213> ORGANISM: Rattus norvegicus

<400> SEQUENCE: 2

```
Met Arg Phe Asn Gly Lys Ser Gly Val Glu Val Arg Leu Pro Asn Asp
1               5                   10                  15

Leu Glu Asp Leu Lys Gly Tyr Thr Ser Leu Ser Leu Phe Leu Gln Arg
            20                  25                  30

Pro Asp Leu Arg Glu Asn Gly Gly Thr Glu Asp Met Phe Val Met Tyr
        35                  40                  45

Leu Gly Asn Lys Asp Ala Ser Lys Asp Tyr Ile Gly Met Ala Val Val
    50                  55                  60

Asp Gly Gln Leu Thr Cys Val Tyr Asn Leu Gly Asp Arg Glu Ala Glu
65                  70                  75                  80

Val Gln Ile Asp Gln Val Leu Thr Glu Ser Glu Ser Gln Glu Ala Val
            85                  90                  95

Met Asp Arg Val Lys Phe Gln Arg Ile Tyr Gln Phe Ala Lys Leu Asn
            100                 105                 110

Tyr Thr Lys Glu Ala Thr Ser Asn Lys Pro Lys Ala Pro Ala Val Tyr
        115                 120                 125

Asp Leu Glu Gly Gly Ser Ser Asn Thr Leu Leu Asn Leu Asp Pro Glu
    130                 135                 140

Asp Ala Val Phe Tyr Val Gly Tyr Pro Pro Asp Phe Glu Leu Pro
145                 150                 155                 160

Ser Arg Leu Arg Phe Pro Pro Tyr Lys Gly Cys Ile Glu Leu Asp Asp
            165                 170                 175

Leu Asn Glu Asn Val Leu Ser Leu Tyr Asn Phe Lys Thr Thr Phe Asn
        180                 185                 190
```

```
Leu Asn Thr Thr Glu Val Glu Pro Cys Arg Arg Lys Glu Glu Ser
        195                 200                 205

Asp Lys Asn Tyr Phe Glu Gly Thr Gly Tyr Ala Arg Ile Pro Thr Gln
    210                 215                 220

Pro Asn Ala Pro Phe Pro Asn Phe Ile Gln Thr Ile Gln Thr Thr Val
225                 230                 235                 240

Asp Arg Gly Leu Leu Phe Phe Ala Glu Asn Gln Asp Asn Phe Ile Ser
                245                 250                 255

Leu Asn Ile Glu Asp Gly Asn Leu Met Val Arg Tyr Lys Leu Asn Ser
            260                 265                 270

Glu Pro Pro Lys Glu Lys Gly Ile Arg Asp Thr Ile Asn Asp Gly Lys
        275                 280                 285

Asp His Ser Ile Leu Ile Thr Ile Gly Lys Leu Gln Lys Arg Met Trp
    290                 295                 300

Ile Asn Val Asn Glu Arg Ser Val Arg Ile Glu Gly Glu Ile Phe Asp
305                 310                 315                 320

Phe Ser Thr Tyr Tyr Leu Gly Gly Ile Pro Ile Ala Ile Arg Glu Arg
                325                 330                 335

Phe Asn Ile Ser Thr Pro Ala Phe Gln Gly Cys Met Lys Asn Leu Lys
            340                 345                 350

Lys Thr Ser Gly Val Val Arg Leu Asn Asp Thr Val Gly Val Thr Lys
        355                 360                 365

Lys Cys Ser Glu Asp Trp Lys Leu Val Arg Thr Ala Ser Phe Ser Arg
    370                 375                 380

Gly Gly Gln Met Ser Phe Thr Asn Leu Asp Val Pro Ser Thr Asp Arg
385                 390                 395                 400

Phe Gln Leu Ser Phe Gly Phe Gln Thr Phe Gln Pro Ser Gly Thr Leu
                405                 410                 415

Leu Asn His Gln Thr Arg Thr Ser Ser Leu Leu Val Thr Leu Glu Asp
            420                 425                 430

Gly His Ile Glu Leu Ser Thr Arg Asp Ser Asn Ile Pro Ile Phe Lys
        435                 440                 445

Ser Pro Gly Thr Tyr Met Asp Gly Leu Leu His His Val Ser Val Ile
    450                 455                 460

Ser Asp Thr Ser Gly Leu Arg Leu Leu Ile Asp Asp Gln Val Leu Arg
465                 470                 475                 480

Arg Asn Gln Arg Leu Pro Ser Phe Ser Asn Ala Gln Gln Ser Leu Arg
                485                 490                 495

Leu Gly Gly Gly His Phe Glu Gly Cys Ile Ser Asn Val Leu Val Gln
            500                 505                 510

Arg Phe Ser Gln Ser Pro Glu Val Leu Asp Leu Ala Ser Lys Ser Thr
        515                 520                 525

Lys Lys Asp Ala Ser Leu Gly Gly Cys Ser Leu Asn Lys Pro Pro Phe
    530                 535                 540

Leu Met Leu Phe Lys Ser Pro Lys Arg Phe Asn Lys Gly Arg Ile Phe
545                 550                 555                 560

Asn Val Asn Gln Leu Met Gln Asp Ala Pro Gln Ala Thr Arg Ser Thr
                565                 570                 575

Glu Ala Trp Gln Asp Gly Arg Ser Cys Leu Pro Pro Leu Asn Thr Lys
            580                 585                 590

Ala Ser His Arg Ala Leu Gln Phe Gly Asp Ser Pro Thr Ser His Leu
        595                 600                 605
```

```
Leu Leu Lys Leu Pro Gln Glu Leu Leu Lys Pro Arg Ser Gln Phe Ser
    610                 615                 620

Leu Asp Ile Gln Thr Thr Ser Pro Lys Gly Leu Val Phe Tyr Ala Gly
625                 630                 635                 640

Thr Lys Asp Ser Phe Leu Ala Leu Tyr Val Ala Asp Gly Arg Val Val
                645                 650                 655

Phe Ala Leu Gly Ala Gly Lys Lys Leu Arg Leu Arg Ser Lys Glu
            660                 665                 670

Arg Tyr His Asp Gly Lys Trp His Thr Val Val Phe Gly Leu Asn Gly
        675                 680                 685

Gly Lys Ala Arg Leu Val Val Asp Gly Leu Arg Ala Gln Glu Gly Ser
    690                 695                 700

Leu Pro Gly Asn Ser Thr Ile Ser Pro Arg Glu Gln Val Tyr Leu Gly
705                 710                 715                 720

Leu Pro Leu Ser Arg Lys Pro Lys Ser Leu Pro Gln His Ser Phe Val
                725                 730                 735

Gly Cys Leu Arg Asp Phe Gln Leu Asn Ser Lys Pro Leu Asp Ser Pro
            740                 745                 750

Ser Ala Arg Phe Gly Val Ser Pro Cys Leu Gly Gly Ser Leu Glu Lys
        755                 760                 765

Gly Ile Tyr Phe Ser Gln Gly Gly His Val Ile Leu Ala Asn Ser
    770                 775                 780

Val Ser Leu Gly Pro Glu Leu Lys Leu Thr Phe Ser Ile Arg Pro Arg
785                 790                 795                 800

Ser Leu Thr Gly Val Leu Ile His Val Gly Ser Gln Ser Gly Gln Arg
                805                 810                 815

Leu Ser Val Tyr Met Glu Ala Gly Lys Val Thr Thr Ser Val Ser Ser
            820                 825                 830

Asp Ala Gly Gly Ser Val Thr Ser Ile Thr Pro Lys Gln Ser Leu Cys
        835                 840                 845

Asp Gly Gln Trp His Ser Val Ala Val Ser Ile Lys Gln Arg Ile Leu
    850                 855                 860

His Leu
865

<210> SEQ ID NO 3
<211> LENGTH: 1743
<212> TYPE: DNA
<213> ORGANISM: Rattus norvegicus
<220> FEATURE:
<221> NAME/KEY: CDS
<222> LOCATION: (49)..(1743)

<400> SEQUENCE: 3
gagctcattc agcaggccag agatgctgcg aacaaggttg caattccc atg agg ttc      57
                                                    Met Arg Phe
                                                      1 aat ggt aaa tct ggt gtt gaa gtc cgt ctg cca aat gac cta gaa gac     105
Asn Gly Lys Ser Gly Val Glu Val Arg Leu Pro Asn Asp Leu Glu Asp
      5                  10                  15 ttg aag gga tac acg tct ctg tct ttg ttc ctc caa aga cca gac tta     153
Leu Lys Gly Tyr Thr Ser Leu Ser Leu Phe Leu Gln Arg Pro Asp Leu
 20                  25                  30                  35 aga gag aat gga ggc act gag gac atg ttt gta atg tac ctt gga aac     201
Arg Glu Asn Gly Gly Thr Glu Asp Met Phe Val Met Tyr Leu Gly Asn
                 40                  45                  50
```

```
                                              -continued aag gat gcc tcc aag gac tac atc ggc atg gcg gtt gta gat ggc cag        249
Lys Asp Ala Ser Lys Asp Tyr Ile Gly Met Ala Val Val Asp Gly Gln
             55                  60                  65 ctg acg tgt gtc tac aac ctg ggg gac cga gaa gct gaa gtt cag atc        297
Leu Thr Cys Val Tyr Asn Leu Gly Asp Arg Glu Ala Glu Val Gln Ile
     70                  75                  80 gat cag gtc ctg acg gag agt gag tct cag gag gca gtt atg gac cgg        345
Asp Gln Val Leu Thr Glu Ser Glu Ser Gln Glu Ala Val Met Asp Arg
 85                  90                  95 gtg aag ttc cag aga ata tat caa ttt gcc aag ctt aat tac acc aaa        393
Val Lys Phe Gln Arg Ile Tyr Gln Phe Ala Lys Leu Asn Tyr Thr Lys
100                 105                 110                 115 gaa gcc acg tcc aat aaa ccc aaa gct ccc gcg gtc tac gac ctg gag        441
Glu Ala Thr Ser Asn Lys Pro Lys Ala Pro Ala Val Tyr Asp Leu Glu
             120                 125                 130 ggt ggc agt agc aac acg ctc ctt aat ttg gat ccc gag gac gct gtg        489
Gly Gly Ser Ser Asn Thr Leu Leu Asn Leu Asp Pro Glu Asp Ala Val
         135                 140                 145 ttt tat gtc gga ggt tac cca ccg gat ttt gaa ctt cct agc aga ctg        537
Phe Tyr Val Gly Gly Tyr Pro Pro Asp Phe Glu Leu Pro Ser Arg Leu
     150                 155                 160 cgg ttc cct cca tac aaa ggc tgt atc gaa cta gat gac ctc aat gaa        585
Arg Phe Pro Pro Tyr Lys Gly Cys Ile Glu Leu Asp Asp Leu Asn Glu
165                 170                 175 aac gtt cta agc ttg tac aat ttc aag aca act ttc aat ctc aac acc        633
Asn Val Leu Ser Leu Tyr Asn Phe Lys Thr Thr Phe Asn Leu Asn Thr
180                 185                 190                 195 acg gag gtg gag cct tgt agg agg aga aag gaa gag tca gac aaa aat        681
Thr Glu Val Glu Pro Cys Arg Arg Arg Lys Glu Glu Ser Asp Lys Asn
             200                 205                 210 tac ttt gaa ggt aca ggc tat gct cgc atc cct act caa cca aat gct        729
Tyr Phe Glu Gly Thr Gly Tyr Ala Arg Ile Pro Thr Gln Pro Asn Ala
         215                 220                 225 ccc ttc cca aac ttc ata cag acc atc cag act act gtg gac aga ggt        777
Pro Phe Pro Asn Phe Ile Gln Thr Ile Gln Thr Thr Val Asp Arg Gly
     230                 235                 240 tta ctg ttc ttc gca gaa aac cag gat aac ttc ata tct ctg aac ata        825
Leu Leu Phe Phe Ala Glu Asn Gln Asp Asn Phe Ile Ser Leu Asn Ile
245                 250                 255 gaa gat ggc aat ctc atg gtg aga tac aaa cta aat tca gag cca ccc        873
Glu Asp Gly Asn Leu Met Val Arg Tyr Lys Leu Asn Ser Glu Pro Pro
260                 265                 270                 275 aaa gag aag gga att cga gac acc atc aac gat ggg aaa gat cat tcg        921
Lys Glu Lys Gly Ile Arg Asp Thr Ile Asn Asp Gly Lys Asp His Ser
             280                 285                 290 atc tta atc aca att gga aaa cta caa aaa cgc atg tgg ata aat gtg        969
Ile Leu Ile Thr Ile Gly Lys Leu Gln Lys Arg Met Trp Ile Asn Val
         295                 300                 305 aac gaa cgc agt gta cga atc gaa ggg gaa ata ttt gat ttc agc aca       1017
Asn Glu Arg Ser Val Arg Ile Glu Gly Glu Ile Phe Asp Phe Ser Thr
     310                 315                 320 tat tat ttg ggc gga att cca att gca atc aga gaa agg ttt aac atc       1065
Tyr Tyr Leu Gly Gly Ile Pro Ile Ala Ile Arg Glu Arg Phe Asn Ile
325                 330                 335 tca acg cct gct ttc caa ggc tgc atg aag aat ctg aag aaa acc agt       1113
Ser Thr Pro Ala Phe Gln Gly Cys Met Lys Asn Leu Lys Lys Thr Ser
340                 345                 350                 355 ggg gtt gtc agg ttg aat gat act gtg ggt gta acc aag aag tgc tca       1161
Gly Val Val Arg Leu Asn Asp Thr Val Gly Val Thr Lys Lys Cys Ser
             360                 365                 370
```

```
gaa gac tgg aag ctt gtg cga acc gcc tcg ttc tcc aga gga ggg cag    1209
Glu Asp Trp Lys Leu Val Arg Thr Ala Ser Phe Ser Arg Gly Gly Gln
        375                 380                 385 atg agc ttt aca aac ttg gac gtg ccc tcg act gac cgc ttc cag ctc    1257
Met Ser Phe Thr Asn Leu Asp Val Pro Ser Thr Asp Arg Phe Gln Leu
390                 395                 400 tcc ttt ggg ttt cag acc ttt caa ccc agt ggc aca ctg ctc aat cat    1305
Ser Phe Gly Phe Gln Thr Phe Gln Pro Ser Gly Thr Leu Leu Asn His
    405                 410                 415 cag acg cgg aca agc agc ctg ctg gtc acc ctg gaa gat ggg cac att    1353
Gln Thr Arg Thr Ser Ser Leu Leu Val Thr Leu Glu Asp Gly His Ile
420                 425                 430                 435 gag ttg agc act agg gac agc aac atc cca att ttc aag tct cca ggg    1401
Glu Leu Ser Thr Arg Asp Ser Asn Ile Pro Ile Phe Lys Ser Pro Gly
            440                 445                 450 acc tac atg gac ggt tta ctg cat cat gta tct gta ata agt gac acc    1449
Thr Tyr Met Asp Gly Leu Leu His His Val Ser Val Ile Ser Asp Thr
            455                 460                 465 tca ggt ctc cgc ctt ctc atc gat gac cag gtc ctg aga agg aac cag    1497
Ser Gly Leu Arg Leu Leu Ile Asp Asp Gln Val Leu Arg Arg Asn Gln
    470                 475                 480 agg ctt cct agc ttc tct aac gcc cag cag tcg ctc cgc ctt gga gga    1545
Arg Leu Pro Ser Phe Ser Asn Ala Gln Gln Ser Leu Arg Leu Gly Gly
485                 490                 495 ggt cat ttc gag ggt tgt atc agc aat gtt tta gtc caa agg ttt tca    1593
Gly His Phe Glu Gly Cys Ile Ser Asn Val Leu Val Gln Arg Phe Ser
500                 505                 510                 515 cag agt cca gaa gtc ctg gat ctg gcc agt aaa tct acc aag aag gat    1641
Gln Ser Pro Glu Val Leu Asp Leu Ala Ser Lys Ser Thr Lys Lys Asp
                520                 525                 530 gca tcc cta gga ggc tgc agt tta aac aag cca cct ttt ctt atg ttg    1689
Ala Ser Leu Gly Gly Cys Ser Leu Asn Lys Pro Pro Phe Leu Met Leu
            535                 540                 545 ttt aaa agt ccc aag aga ttt aac aag ggc cgg att ttc aat gtt aat    1737
Phe Lys Ser Pro Lys Arg Phe Asn Lys Gly Arg Ile Phe Asn Val Asn
        550                 555                 560 cag ctg                                                            1743
Gln Leu
    565

<210> SEQ ID NO 4
<211> LENGTH: 565
<212> TYPE: PRT
<213> ORGANISM: Rattus norvegicus

<400> SEQUENCE: 4

Met Arg Phe Asn Gly Lys Ser Gly Val Glu Val Arg Leu Pro Asn Asp
1               5                   10                  15

Leu Glu Asp Leu Lys Gly Tyr Thr Ser Leu Ser Leu Phe Leu Gln Arg
            20                  25                  30

Pro Asp Leu Arg Glu Asn Gly Gly Thr Glu Asp Met Phe Val Met Tyr
        35                  40                  45

Leu Gly Asn Lys Asp Ala Ser Lys Asp Tyr Ile Gly Met Ala Val Val
    50                  55                  60

Asp Gly Gln Leu Thr Cys Val Tyr Asn Leu Gly Asp Arg Glu Ala Glu
65                  70                  75                  80

Val Gln Ile Asp Gln Val Leu Thr Glu Ser Glu Ser Gln Glu Ala Val
                85                  90                  95
```

```
Met Asp Arg Val Lys Phe Gln Arg Ile Tyr Gln Phe Ala Lys Leu Asn
            100                 105                 110
Tyr Thr Lys Glu Ala Thr Ser Asn Lys Pro Lys Ala Pro Ala Val Tyr
        115                 120                 125
Asp Leu Glu Gly Gly Ser Ser Asn Thr Leu Leu Asn Leu Asp Pro Glu
    130                 135                 140
Ala Ala Val Phe Tyr Val Gly Tyr Pro Pro Asp Phe Glu Leu Pro
145                 150                 155                 160
Ser Arg Leu Arg Phe Pro Pro Tyr Lys Gly Cys Ile Glu Leu Asp Asp
                165                 170                 175
Leu Asn Glu Asn Val Leu Ser Leu Tyr Asn Phe Lys Thr Thr Phe Asn
            180                 185                 190
Leu Asn Thr Thr Glu Val Glu Pro Cys Arg Arg Arg Lys Glu Ser
        195                 200                 205
Asp Lys Asn Tyr Phe Glu Gly Thr Gly Tyr Ala Arg Ile Pro Thr Gln
    210                 215                 220
Pro Asn Ala Pro Phe Pro Asn Phe Ile Gln Thr Ile Gln Thr Thr Val
225                 230                 235                 240
Asp Arg Gly Leu Leu Phe Phe Ala Glu Asn Gln Asp Asn Phe Ile Ser
                245                 250                 255
Leu Asn Ile Glu Asp Gly Asn Leu Met Val Arg Tyr Lys Leu Asn Ser
            260                 265                 270
Glu Pro Pro Lys Glu Lys Gly Ile Arg Asp Thr Ile Asn Asp Gly Lys
        275                 280                 285
Asp His Ser Ile Leu Ile Thr Ile Gly Lys Leu Gln Lys Arg Met Trp
    290                 295                 300
Ile Asn Val Asn Glu Arg Ser Val Arg Ile Glu Gly Glu Ile Phe Asp
305                 310                 315                 320
Phe Ser Thr Tyr Tyr Leu Gly Gly Ile Pro Ile Ala Ile Arg Glu Arg
                325                 330                 335
Phe Asn Ile Ser Thr Pro Ala Phe Gln Gly Cys Met Lys Asn Leu Lys
            340                 345                 350
Lys Thr Ser Gly Val Val Arg Leu Asn Asp Thr Val Gly Val Thr Lys
        355                 360                 365
Lys Cys Ser Glu Asp Trp Lys Leu Val Arg Thr Ala Ser Phe Ser Arg
    370                 375                 380
Gly Gly Gln Met Ser Phe Thr Asn Leu Asp Val Pro Ser Thr Asp Arg
385                 390                 395                 400
Phe Gln Leu Ser Phe Gly Phe Gln Thr Phe Gln Pro Ser Gly Thr Leu
                405                 410                 415
Leu Asn His Gln Thr Arg Thr Ser Ser Leu Leu Val Thr Leu Glu Asp
            420                 425                 430
Gly His Ile Glu Leu Ser Thr Arg Asp Ser Asn Ile Pro Ile Phe Lys
        435                 440                 445
Ser Pro Gly Thr Tyr Met Asp Gly Leu Leu His Val Ser Val Ile
    450                 455                 460
Ser Asp Thr Ser Gly Leu Arg Leu Leu Ile Asp Asp Gln Val Leu Arg
465                 470                 475                 480
Arg Asn Gln Arg Leu Pro Ser Phe Ser Asn Ala Gln Gln Ser Leu Arg
                485                 490                 495
Leu Gly Gly Gly His Phe Glu Gly Cys Ile Ser Asn Val Leu Val Gln
            500                 505                 510
```

```
                       Arg Phe Ser Gln Ser Pro Glu Val Leu Asp Leu Ala Ser Lys Ser Thr
                               515                 520                 525

Lys Lys Asp Ala Ser Leu Gly Gly Cys Ser Leu Asn Lys Pro Pro Phe
                           530                 535                 540

Leu Met Leu Phe Lys Ser Pro Lys Arg Phe Asn Lys Gly Arg Ile Phe
                       545                 550                 555                 560

Asn Val Asn Gln Leu
                                       565

<210> SEQ ID NO 5
<211> LENGTH: 713
<212> TYPE: DNA
<213> ORGANISM: Rattus norvegicus
<220> FEATURE:
<221> NAME/KEY: CDS
<222> LOCATION: (60)..(713)

<400> SEQUENCE: 5
gaattccaat tgcaatcaga gaaaggttta acatctcaac gcctgctttc caaggctgc         59 atg aag aat ctg aag aaa acc agt ggg gtt gtc agg ttg aat gat act        107
Met Lys Asn Leu Lys Lys Thr Ser Gly Val Val Arg Leu Asn Asp Thr
 1               5                  10                  15 gtg ggt gta acc aag aag tgc tca gaa gac tgg aag ctt gtg cga acc        155
Val Gly Val Thr Lys Lys Cys Ser Glu Asp Trp Lys Leu Val Arg Thr
             20                  25                  30 gcc tcg ttc tcc aga gga ggg cag atg agc ttt aca aac ttg gac gtg        203
Ala Ser Phe Ser Arg Gly Gly Gln Met Ser Phe Thr Asn Leu Asp Val
         35                  40                  45 ccc tcg act gac cgc ttc cag ctc tcc ttt ggg ttt cag acc ttt caa        251
Pro Ser Thr Asp Arg Phe Gln Leu Ser Phe Gly Phe Gln Thr Phe Gln
     50                  55                  60 ccc agt ggc aca ctg ctc aat cat cag acg cgg aca agc agc ctg ctg        299
Pro Ser Gly Thr Leu Leu Asn His Gln Thr Arg Thr Ser Ser Leu Leu
 65                  70                  75                  80 gtc acc ctg gaa gat ggg cac att gag ttg agc act agg gac agc aac        347
Val Thr Leu Glu Asp Gly His Ile Glu Leu Ser Thr Arg Asp Ser Asn
                 85                  90                  95 atc cca att ttc aag tct cca ggg acc tac atg gac ggt tta ctg cat        395
Ile Pro Ile Phe Lys Ser Pro Gly Thr Tyr Met Asp Gly Leu Leu His
            100                 105                 110 cat gta tct gta ata agt gac acc tca ggt ctc cgc ctt ctc atc gat        443
His Val Ser Val Ile Ser Asp Thr Ser Gly Leu Arg Leu Leu Ile Asp
        115                 120                 125 gac cag gtc ctg aga agg aac cag agg ctt cct agc ttc tct aac gcc        491
Asp Gln Val Leu Arg Arg Asn Gln Arg Leu Pro Ser Phe Ser Asn Ala
    130                 135                 140 cag cag tcg ctc cgc ctt gga gga ggt cat ttc gag ggt tgt atc agc        539
Gln Gln Ser Leu Arg Leu Gly Gly Gly His Phe Glu Gly Cys Ile Ser
145                 150                 155                 160 aat gtt tta gtc caa agg ttt tca cag agt cca gaa gtc ctg gat ctg        587
Asn Val Leu Val Gln Arg Phe Ser Gln Ser Pro Glu Val Leu Asp Leu
                165                 170                 175 gcc agt aaa tct acc aag aag gat gca tcc cta gga ggc tgc agt tta        635
Ala Ser Lys Ser Thr Lys Lys Asp Ala Ser Leu Gly Gly Cys Ser Leu
            180                 185                 190
```

```
aac aag cca cct ttt ctt atg ttg ttt aaa agt ccc aag aga ttt aac    683
Asn Lys Pro Pro Phe Leu Met Leu Phe Lys Ser Pro Lys Arg Phe Asn
        195                 200                 205 aag ggc cgg att ttc aat gtt aat cag ctg                            713
Lys Gly Arg Ile Phe Asn Val Asn Gln Leu
    210                 215

<210> SEQ ID NO 6
<211> LENGTH: 218
<212> TYPE: PRT
<213> ORGANISM: Rattus norvegicus

<400> SEQUENCE: 6

Met Lys Asn Leu Lys Lys Thr Ser Gly Val Val Arg Leu Asn Asp Thr
 1               5                  10                  15

Val Gly Val Thr Lys Lys Cys Ser Glu Asp Trp Lys Leu Val Arg Thr
            20                  25                  30

Ala Ser Phe Ser Arg Gly Gly Gln Met Ser Phe Thr Asn Leu Asp Val
        35                  40                  45

Pro Ser Thr Asp Arg Phe Gln Leu Ser Phe Gly Phe Gln Thr Phe Gln
    50                  55                  60

Pro Ser Gly Thr Leu Leu Asn His Gln Thr Arg Thr Ser Ser Leu Leu
65                  70                  75                  80

Val Thr Leu Glu Asp Gly His Ile Glu Leu Ser Thr Arg Asp Ser Asn
                85                  90                  95

Ile Pro Ile Phe Lys Ser Pro Gly Thr Tyr Met Asp Gly Leu Leu His
            100                 105                 110

His Val Ser Val Ile Ser Asp Thr Ser Gly Leu Arg Leu Leu Ile Asp
        115                 120                 125

Asp Gln Val Leu Arg Arg Asn Gln Arg Leu Pro Ser Phe Ser Asn Ala
    130                 135                 140

Gln Gln Ser Leu Arg Leu Gly Gly Gly His Phe Glu Gly Cys Ile Ser
145                 150                 155                 160

Asn Val Leu Val Gln Arg Phe Ser Gln Ser Pro Glu Val Leu Asp Leu
                165                 170                 175

Ala Ser Lys Ser Thr Lys Lys Asp Ala Ser Leu Gly Gly Cys Ser Leu
            180                 185                 190

Asn Lys Pro Pro Phe Leu Met Leu Phe Lys Ser Pro Lys Arg Phe Asn
        195                 200                 205

Lys Gly Arg Ile Phe Asn Val Asn Gln Leu
    210                 215

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aattaaccct cactaaaggg                                               20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 8
taatacgact cactataggg                                              20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccagactact gtggacagag g                                            21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aagggttctt cgtgtgtagg g                                            21

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctactcaacc aaatgctccc                                              20

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gtactattca acctgacaac cc                                           22

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gactggttcc aattgacaag c                                            21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
-continued
<400> SEQUENCE: 14
gcaaatggca ttctgacatc c                                              21
```